United States Patent
Waller et al.

(10) Patent No.: US 11,464,855 B2
(45) Date of Patent: *Oct. 11, 2022

(54) ANTAGONISM OF THE VIP SIGNALING PATHWAY

(71) Applicant: Emory University, Atlanta, GA (US)

(72) Inventors: Edmund K. Waller, Atlanta, GA (US); Jian-Ming Li, Atlanta, GA (US); Mohammad S. Hossain, Lilburn, GA (US)

(73) Assignee: Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/601,352

(22) Filed: May 22, 2017

(65) Prior Publication Data

US 2017/0258904 A1    Sep. 14, 2017

Related U.S. Application Data

(62) Division of application No. 13/979,003, filed as application No. PCT/US2012/023268 on Jan. 31, 2012, now Pat. No. 9,669,092.

(60) Provisional application No. 61/467,714, filed on Mar. 25, 2011, provisional application No. 61/438,707, filed on Feb. 2, 2011.

(51) Int. Cl.
| | |
|---|---|
| *A61K 38/00* | (2006.01) |
| *A61P 35/02* | (2006.01) |
| *A61K 38/22* | (2006.01) |
| *C07K 14/575* | (2006.01) |
| *A61K 38/16* | (2006.01) |
| *C12N 5/071* | (2010.01) |
| *A61K 39/395* | (2006.01) |
| *C12N 5/0789* | (2010.01) |
| *C12N 5/0775* | (2010.01) |
| *C12N 5/078* | (2010.01) |
| *A61K 35/14* | (2015.01) |
| *A61K 35/17* | (2015.01) |
| *A61K 38/04* | (2006.01) |
| *A61K 39/245* | (2006.01) |

(52) U.S. Cl.
CPC .......... *A61K 39/3955* (2013.01); *A61K 35/14* (2013.01); *A61K 35/17* (2013.01); *A61K 38/04* (2013.01); *A61K 38/16* (2013.01); *A61K 38/2278* (2013.01); *A61K 39/245* (2013.01); *A61P 35/02* (2018.01); *C12N 5/0634* (2013.01); *C12N 5/0647* (2013.01); *C12N 5/0662* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,217,953 A | 6/1993 | Gozes | |
| 5,565,424 A | 10/1996 | Gozes | |
| 6,630,124 B1* | 10/2003 | Gozes | A61K 31/351 424/1.69 |
| 6,828,304 B1 | 12/2004 | Burman | |
| 7,094,755 B2 | 8/2006 | Burman | |
| 9,458,217 B2 | 10/2016 | Waller | |
| 9,669,092 B2 | 6/2017 | Waller | |
| 2003/0158110 A1 | 8/2003 | Burman | |
| 2004/0092583 A1 | 5/2004 | Shanahan | |
| 2006/0223748 A1 | 10/2006 | Bevec | |
| 2010/0006204 A1 | 1/2010 | Burke | |
| 2013/0130379 A1 | 5/2013 | Adams | |

FOREIGN PATENT DOCUMENTS

| | | |
|---|---|---|
| CA | 2197139 | 2/1998 |
| WO | 2001093889 | 12/2001 |
| WO | 2009039991 | 4/2009 |

OTHER PUBLICATIONS

Hamadani et al., Biol. Blood Marrow Transplantation 14:556-567 (2008) (Year: 2008).*
Krause et al., Cell 105:369-377 (2001) (Year: 2001).*
Gozes et al., Best Practice & Res. Clin. Endocrin. Metab. 18:623-640 (2004) (Year: 2004).*
OSI Pharm. v. Apotex Inc., Federal Circuit, 20 pages (2019) (Year: 2019).*
Mirabelli et al., Cancers 11:1-18 (2019) (Year: 2019).*
"Treatment", Medical Dictionary, available online at https://medical-dictionary.thefreedictionary.com/treatment, 4 pages (accessed on Nov. 20, 2020) (Year: 2020).*
Kummar et al., Br. J. Clin. Pharmacol. 62:15-26 (2006) (Year: 2006).*
National Institute of Health, "5. Hematopoietic Stem Cells," available online at https://stemcells.nih.gov/info/2001report/chapter5.htm, 14 page (2001) (Year: 2001).*
Janeway CA Jr, et al., Immunobiology: The Immune System in Health and Disease. 5th edition. New York: Garland Science; 2001. Generation of lymphocytes in bone marrow and thymus. Available from: https://www.ncbi.nlm.nih.gov/books/NBK27123/ (Year: 2001).*
Warren et al., Blood 91:2197-2207 (1998) (Year: 1998).*
Brentjens, Cellular therapies in acute lymphoblastic leukemia, Curr Opin Mol Ther. 2009, 11(4): 375-382.

(Continued)

*Primary Examiner* — Thea D' Ambrosio
(74) *Attorney, Agent, or Firm* — Meunier Carlin & Curfman LLC

(57) ABSTRACT

Inhibition of the VIP signaling pathway with VIP antagonist is contemplated. In certain embodiments, the disclosure relates to methods of enhancing the immune response to a cell therapy comprising administering a VIP antagonist to a subject in combination with a cell. In certain embodiments, the subject is diagnosed with leukemia or lymphoma. In certain embodiments, the cell is a blood cell, bone marrow cell, leukocyte, T-cell, natural killer cell, a hematopoietic stem cell, a G-CSF mobilized or non-mobilized blood mononuclear cell.

7 Claims, 13 Drawing Sheets

Specification includes a Sequence Listing.

(56) References Cited

OTHER PUBLICATIONS

Cantoni et al. Evidence for a Bidirectional Relationship between Cytomegalovirus Replication and acute Graft-versus-Host Disease, Biol Blood Marrow Transplant 16: 1309-1314 (2010).
Coppola et al. Ablation of TrkA function in the immune system causes B cell abnormalities, Development 131, 5185-5195, (2004).
Dorsam et al. Vasoactive intestinal peptide signaling axis in human leukemia, World J Biol Chem 2011, 2(6): 146-160.
Dudley et al. Generation of Tumor-Infiltrating Lymphocyte Cultures for Use in Adoptive Transfer Therapy for Melanoma Patients, J Immunother. 2003; 26(4): 332-342.
Ellis et al. The effects of vasoactive intestinal peptide (VIP) antagonists, and VIP and peptide histidine isoleucine antisera on non-adrenergic, non-cholinergic relaxations of tracheal smooth muscle, Br. J. Pharmacol. (1989), 96, 513-520.
Emilie et al. Vasoactive intestinal peptide receptor 1 is downregulated during expansion of antigen-specific CD8 T cells following primary and secondary Listeria monocytogenes infections, Journal of Neuroimmunology 234 (2011) 40-48.
Fang et al. A Convenient Approach to Synthesizing Peptide C-Terminal N-Alkyl Amides, Biopolymers. 2011; 96(6): 715-722.
Gonzalez et al. Vasoactive intestinal peptide and regulatory T-cell induction: a new mechanism and therapeutic potential for immune homeostasis, TRENDS in Molecular Medicine vol. 13 No.6, 242-251, (2007).
Gozes et al. A VIP Hybrid Antagonist: From Developmental Neurobiology to Clinical Applications, Cellular and Molecular Neurobiology, 15(6), 675-687, 1995.
Hayez et al. The neuropeptides vasoactive intestinal peptide (VIP) and pituitary adenylate cyclase activating polypeptide (PACAP) modulate several biochemical pathways in human leukemic myeloid cells, Journal of Neuroimmunology 149 (2004) 167-181.
Hill et al. Allogeneic Stem Cell Transplantation with Peripheral Blood Stem Cells Mobilized by Pegylated G-CSF, Biology of Blood and Marrow Transplantation 12:603-607 (2006).
Hossain et al. Chronic GvHD decreases antiviral immune responses in allogeneic BMT, Blood, 2007, 109(10) 4548-4556.
Hossain et al. PD-1 and CTLA-4 up regulation on donor T cells is insufficient to prevent GvHD in allo-HSCT recipients, PLoS ONE 12(9): e01842546, (2017).
Kamar et al. Predictive Factors for Cytomegalovirus Reactivation in Cytomegalovirus-Seropositive Kidney-Transplant Patients, J. Med. Virol. 80:1012-1017, 2008.
Kantoff et al. Sipuleucel-T Immunotherapy for Castration-Resistant Prostate Cancer, N Engl J Med 2010, 363:411-22.
Kordasti et al. Serotonin and vasoactive intestinal peptide antagonists attenuate rotavirus diarrhoea, Gut 2004, 53:952-957.
Li et al. Blocking Vasoactive Intestinal Peptide Signaling Enhances Anti-Viral Immunity without Increased Graft Versus Host fdisease in Murine Allogeneic Bone Marrow Transplantation, Abstract at the 53rd Annual Meeting and Exposition of the American-Society-of-Hematology (ASH); San Diego, CA, USA; Dec. 10-13, 2011.
Li et al. Absence of Vasoactive Intestinal Peptide Expression in Hematopoietic Cells Enhances Th1 Polarization and Antiviral Immunity in Mice, J Immunol 2011; 187:1057-1065.
Li et al. The Absence of Vasoactive Intestinal Peptide Augments Alloreactivity and the Anti-Viral Response in a Bone Marrow Transplant Setting, Journal of the American Society for Blood and Marrow Transplantation, 2010, vol. 16, Issue 2, Supplement 2, pp. S223-S224.
Li et al. Blocking VIP Signaling during Allogenic Bone Marrow Transplantation Separates the Graft Verse Leukemia from Graft Versus Host Disease Activity of Donor CD8 T-Cells, Blood 2015 126:1877.
Li et al. Modulation of Immune Checkpoints and Graft-versus-Leukemia in Allogenic Transplants by Antagonizing Vasoactive Intestinal Peptide Signaling, Cancer Res; 76(23), 6802-15, (2016).
Lilja et al., The next generation recombinant human cytomegalovirus vaccine candidates—Beyond gB, Vaccine 30 (2012) 6980-6990.

Moody et al. A vasoactive intestinal peptide antagonist inhibits non-small cell lung cancer growth, Proc. Natl. Acad. Sci. USA vol. 90, pp. 4345-4349, 1993.
Moody et al. (Stearyl, Norleucine17)VIP Hybrid Antagonizes VIP Receptors on Non-Small Cell Lung Cancer Cells, Life Sciences, vol. 61, No. 17, pp. 1657-1666, 1997.
Moody et al. VIP receptor antagonists and chemotherapeutic drugs inhibit the growth of breast cancer cells, Breast Cancer Research and Treatment 68: 55-64, 2001.
Moody et al. VIP as a trophic factor in the CNS and cancer cells, Peptides 24 (2003) 163-177.
Onoue et al. Structure-activity relationship of vasoactive intestinal peptide (VIP): potent agonists and potential clinical applications, Naunyn-Schmiedebcrg's Arch Pharmacol (2008) 377:579-590.
Peruzzi et al. Inhibition of Natural Killer Cell Cytotoxicity and Interferon gama Production by the Envelope Protein of HIV and Prevention by Vasoactive Intestinal Peptide, AIDS Research and Human Retroviruses vol. 16, No. 11, 2000, pp. 1067-1073.
Plonowski et al. Inhibition of PC-3 Human Prostate Cancers by Analogs of Growth Hormone-Releasing Hormone (GH-RH) Endowed With Vasoactive Intestinal Peptide (VIP) Antagonistic Activity, Int. J. Cancer: 98, 624-629 (2002).
Redwine et al. Peptide T Blocks GP120/CCR5 Chemokine Receptor-Mediated Chemotaxis, Clinical Immunology vol. 93, No. 2, November, pp. 124-131, 1999.
Southerland et al. The Absence of Vasoactive Intestinal Peptide Augments Allo-Reactivity and the Anti-Viral Response in Bone Marrow Transplantation, Blood, 2007, 110:3267.
Thermos, N-Terminal Acetylation and C-Terminal Amidation of Peptides, 2004.
Waller et al. Antagonism of vasoactive intestinal peptide activity stimulates anti-viral immunity and protects transplant recipients from murine cytomegalovirus infection, 37th Annual Meeting of the European Group for Blood and Marrow Transplantation, 2011.
White, Proteins, peptides and amino acid sourcebook, 2002, pp. 435-437.
Yuan et al. Breaking Human Cytomegalovirus Major Immediate-Early Gene Silence by Vasoactive Intestinal Peptide Stimulation of the Protein Kinase A-CREB-TORC2 Signaling Cascade in Human Pluripotent Embryonal NTera2 Cells, Journal of Virology, Jul. 2009, p. 6391-6403.
Zhilinskaia et al. Detection in the structure of influenza viral proteins of sequences similar to vasoactive intestinal peptide, Biulleten Eksperimentalnoi Biologii I Meditsiny, 1991, 111(4) 371-3, (abstract only).
Extended European search report for EP Application No. 12789481.4 dated Oct. 26, 2015.
Dranoff, Cytokines in Cancer Pathogenesis and Cancer Therapy, Nat Rev Cancer, 2004, 4(1):11-22.
Gao et al. Clin. Overexpression of PD-L1 Significantly Associates with Tumor Aggressiveness and Postoperative Recurrence in Human Hepatocellular Carcinoma, Cancer Res. 15, 971-979 (2009).
Hamadani et al. Hematopoietic Stem Cell Transplantation in Adults with Acute Myeloid Leukemia, Biology of Blood and Marrow Transplantation 14:556-567 (2008).
Hamadani et al. The evolving role of statins in hematopoietic stem and progenitor cell transplantation, Am J Blood Res 2011;1(1):57-64.
Li et al. Modulation of Immune Checkpoints and Graft-versus-Leukemia in Allogenic Transplants by Antagonizing Vasoactive Intestinal Peptide Signaling, Cancer Res, 2016, 76(23), 6802-15 (Supplemental material).
Mellman et al. Cancer immunotherapy comes of age, Nature, 2011, 480(7378):480-9.
Petersen et al. Administration of a vasoactive intestinal peptide antagonist enhances the autologous anti-leukemia T cell response in murine models of acute leukemia, Oncoimmunology, 2017, vol. 6, No. 5, e1304336.
Extended European search report for EP Application No. 17178437.4 dated Feb. 13, 2018.
Brahmer et al. Safety and Activity of Anti-PD-L1 Antibody in Patients with Advanced Cancer, N Engl J Med 2012, 366:2455-65.

(56) References Cited

OTHER PUBLICATIONS

Fife et al., Interactions between PD-1 and PD-L1 promote tolerance by blocking the TCR-induced stop signal, Nat Immunol, 2009, 10(11):1185-92.
Topalian et al. Safety, Activity, and Immune Correlates of Anti-PD-1 Antibody in Cancer, N Engl J Med 2012, 366:2443-54.

* cited by examiner

ANTAGONISM OF THE VIP SIGNALING PATHWAY

CROSS-REFERENCE TO RELATED APPLICATIONS

This application is a division of U.S. application Ser. No. 13/979,003 filed Jul. 10, 2013, which is the National Stage of International Application No. PCT/US2012/023268 filed Jan. 31, 2012, which claims the benefit of U.S. Provisional Application No. 61/438,707 filed Feb. 2, 2011, and U.S. Provisional Application No. 61/467,714 filed Mar. 25, 2011. The entirety of each of these applications is hereby incorporated by reference for all purposes.

STATEMENT REGARDING FEDERALLY SPONSORED RESEARCH OR DEVELOPMENT

This invention was made with government support under Grant R01CA074364-04A2 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WED)

The Sequence Listing associated with this application is provided in text format in lieu of a paper copy, and is hereby incorporated by reference into the specification. The name of the text file containing the Sequence Listing is 11026USDIV_ST25.txt. The text file is 6 KB, was created on May 22, 2017, and is being submitted electronically via EFS-Web.

BACKGROUND

Cytomegalovirus (CMV) is a herpes viral genus of the Herpesviruses group thought to infect between 50% and 80% of adults in the United States. Herpesviruses share a characteristic ability to remain dormant within the body over long periods. CMV infections typically become more aggressive in patients with a depressed immune system. Patients who receive allogeneic bone marrow transplantation (aBMT) often suffer from a CMV infection due to the immunocompromising effects of treatment. Thus, there is a need to identify methods that manage CMV infections.

Vasoactive intestinal peptide (VIP) is an endogenous polypeptide that modulates both innate and adaptive immunities. The administration of VIP delays the onset, decreases the frequency, and reduces the severity of disease in various experimental models of autoimmune disease such as sepsis, collagen-induced arthritis, Crohn's disease, type-I diabetes, multiple sclerosis, pancreatitis, keratitis, and uveoretinitis. See Gonzalez-Rey, TRENDS in Molecular Medicine (2007) 13(6):241-251. It has been reported that VIP interacts with the external envelope glycoprotein (gp120) of the human immunodeficiency virus (HIV). See Redwine et al., Clin Immunol (1999) 93(2):124-31 and Peruzzi et al., AIDS Res Hum Retroviruses (2000) 16(11):1067-73. VIP is also thought to activate human CMV major immediate-early (MIE) gene expression initiating viral reactivation during latency. See Yuan et al., J Virology (2009) 83(13): 6391-6403.

Emilie et al., J Neuroimmunol., 2011, provide that vasoactive intestinal peptide receptor 1 is downregulated during expansion of antigen-specific CD8 T cells following primary and secondary Listeria monocytogenes infections. References cited herein are not an admission of prior art.

SUMMARY

This disclosure relates to antagonism of the VIP signaling pathway. In certain embodiments, the disclosure relates to methods of treating or preventing a viral infection comprising administering a VIP antagonist to a subject at risk of, exhibiting symptoms of, or diagnosed with a viral infection. In certain embodiments, the subject is immune compromised or the subject is an allogeneic bone marrow transplant donor or recipient. In typical embodiments, the subject is an organ transplant recipient, undergoing hemodialysis, diagnosed with cancer, receiving an immunosuppressive drug, and/or diagnosed with an HIV-infection. In certain embodiments, the disclosure relates to preventing a viral infection in an immunocompromised subject at risk of infection by administering a VIP antagonist and optionally one or more antiviral agents.

In some embodiments, the disclosure relates to the use of a VIP antagonist in the production of an anti-viral medicament for the treatment of a viral infection. In some embodiments, the subject is diagnosed with a chronic viral infection. In certain embodiments, the subject undergoes serological monitoring. In some embodiments, the administration is under conditions such that the viral infection is no longer detected. In some embodiments, the subject is diagnosed with a RNA virus, DNA virus, or retroviruses. In some embodiments, the subject is diagnosed with a virus that is double stranded DNA virus, sense single stranded DNA virus, double stranded RNA virus, sense single stranded RNA virus, antisense single stranded RNA virus, sense single stranded RNA retrovirus or a double stranded DNA retrovirus. In some embodiments, the subject is diagnosed to have a rotavirus, an influenza virus, a herpes virus, a hepatitis virus, or a lentivirus. In some embodiments, titer of the virus in the subject is reduced after the treatment as compared to pre-treatment.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In certain embodiments, the subject is a mammal, typically a human.

In certain embodiments, the VIP antagonist is a peptide or peptide analog or fragment of VIP, or VIP fragment or analog containing one or more D-amino acids, or chimera of VIP, such as VIP(6-28); VIP(10-28); [LyS(1), Pro(2,5), Arg(3,4), Tyr(6)]-VIP; [D-p-Cl-Phe(6), Leu(17)]-VIP; [Acetyl-His(1), D-Phe(2), Lys(15), Arg(16), Leu(27)]-VIP (1-7)/GRF(8-27)-NH2; [Myristoyl-His(1), Lys(12,27,28), Gly(29,30), Thr(31)]-VIP-NH2; [Acetyl-His(1), D-Phe(2), Lys(15), Arg(16), Leu(17)]-VIP; neurotensin(6-11)VIP(7-28); [Acetyl-His(1), D-Phe(2), Lys(15), Leu(17)]VIP(3-7)/GRF(8-27); [Acetyl-His(1), D-Phe(2), Lys(15), Arg(16)] VIP(3-7)/GHF(8-27)-NH2; [Acetyl-Tyr(1), D-Phe(2)]-GRF (1-29)-NH2; [N-stearyl, norleucine17]VIPhybrid; Leu-Met-Tyr-Pro-Thr-Tyr-Leu-Lys; [D-Phe2]VIP; PACAP(6-27); and PACAP(6-38). In certain embodiments, the VIP antagonist is an VIP antibody or antibody fragment with an epitope to VIP or a VIP receptor. In certain embodiments, the disclosure relates to pharmaceutical compositions comprising a VIP antibody or antibody fragment and a pharmaceutically acceptable excipient.

In some embodiments, the disclosure relates to treating or preventing a viral infection by administering a VIP antagonist in combination with a second antiviral agent. In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine. In certain embodiments, the subject is administered a pharmaceutical composition comprising a VIP antagonist and a second antiviral agent.

In certain embodiments, the disclosure relates to treating a subject with a viral infection after infection by administering a VIP antagonist and an immunoglobulin.

In certain embodiments, the disclosure relates to treating or preventing a viral infection by administering a VIP antagonist and a viral vaccine or in the absence of a viral vaccine.

In certain embodiments, the disclosure relates to enhancing the immune response to a vaccine comprising administering a VIP antagonist to a subject in need thereof. Typically, the vaccine is selected from the group of vaccines consisting of herpes zoster vaccine, smallpox vaccine, polio vaccine, pertussis vaccine, influenza vaccine, diphtheria vaccine, tetanus vaccine, meningococcus vaccine, influenza A vaccine including subtype H1N1 vaccine, influenza B vaccine, influenza C vaccine, rotavirus A vaccine, rotavirus B vaccine, rotavirus C vaccine, rotavirus D vaccine, rotavirus E vaccine, SARS coronavirus vaccine, human adenovirus types (HAdV-1 to 55) vaccine, human papillomavirus (HPV) vaccine, parvovirus B19 vaccine, molluscum contagiosum vaccine, JC vaccine, BK vaccine, Merkel cell polyomavirus vaccine, coxsackie A vaccine, norovirus vaccine, Rubella vaccine, lymphocytic choriomeningitis vaccine, yellow fever vaccine, measles vaccine, mumps vaccine, respiratory syncytial vaccine, rinderpest vaccine, California encephalitis vaccine, hantavirus vaccine, rabies vaccine, ebola vaccine, marburg vaccine, herpes simplex virus-1 (HSV-1) vaccine, herpes simplex virus-2 (HSV-2) vaccine, varicella zoster vaccine, Epstein-Barr virus (EBV) vaccine, cytomegalovirus (CMV) vaccine, herpes lymphotropic vaccine, roseolovirus vaccine, Kaposi's sarcoma-associated herpesvirus vaccine, hepatitis A (HAV) vaccine, hepatitis B (HBV) vaccine, hepatitis C (HCV) vaccine, hepatitis D (HDV) vaccine, hepatitis E (HEV) vaccine, human immunodeficiency virus (HIV) vaccine, The Human T-lymphotropic virus Type I (HTLV-1) vaccine, Friend spleen focus-forming virus (SFFV) vaccine, and Xenotropic MuLV-Related Virus (XMRV) vaccine. In certain embodiments, the vaccine for a subject diagnosed with a chronic viral infection.

In certain embodiments, the vaccine comprises a protein or peptide, carbohydrate, sugar, polysaccharide, or nucleic acid. Typically the vaccine is an attenuated replication competent virus or an inactivated virus. In certain embodiments, the vaccine comprises a live or a killed or inactivated prokaryotic or eukaryotic cell.

In certain embodiments, the disclosure relates to methods of enhancing the immune response to a cell therapy comprising administering a VIP antagonist to a subject in combination with a cell. In certain embodiments, the subject is diagnosed with leukemia or lymphoma. In certain embodiments, the cell is a blood cell, bone marrow cell, leukocyte, T-cell, natural killer cell, a hematopoietic stem cell, a G-CSF mobilized or non-mobilized blood mononuclear cell.

In certain embodiments the cell is selected from the group consisting of autologous T-cells, allogeneic cells from a HLA matched donor, or allogeneic cells from a HLA mismatched donor. In certain embodiments, the cell is a bone marrow cell. In certain embodiments, the cell is a blood mononuclear cell comprising/expressing granulocyte colony-stimulating factor. The cell therapy may be conducted with non-mobilized blood mononuclear cells.

DETAILED DISCUSSION

Figure 1:
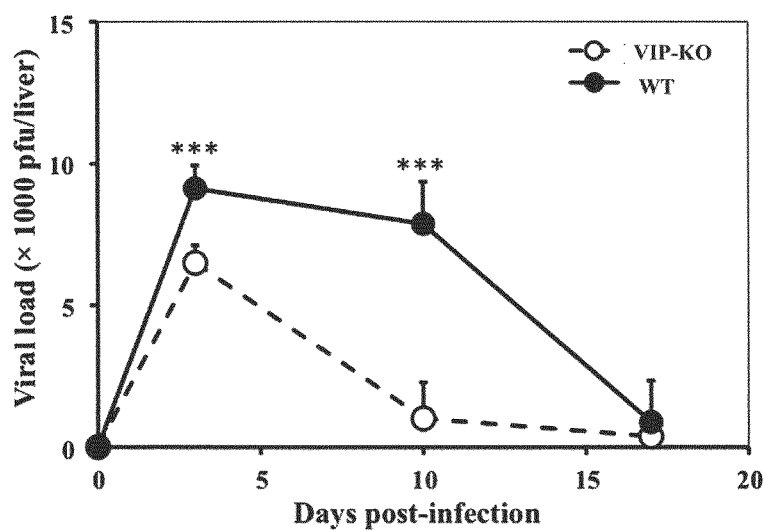
FIG. 1 shows data suggesting mice lacking VIP had lower levels of virus in the liver following mCMV infection. VIP-KO and WT mice were infected (day 0) with low dose $5\times10^4$ PFU mCMV. Livers were collected, weighed, and lysates prepared at days 3, 7, 10, 14 and 17 days post-mCMV infection. Day 0 control livers were from uninfected mice. Liver viral load was measured by plaque assay of a defined quantity of liver lysate on 3T3 cell monolayers, and the number of pfu/liver calculated. *** Signifies $p<0.001$, denoting a significant difference between VIP-KO and WT mice.
Figure 2A:
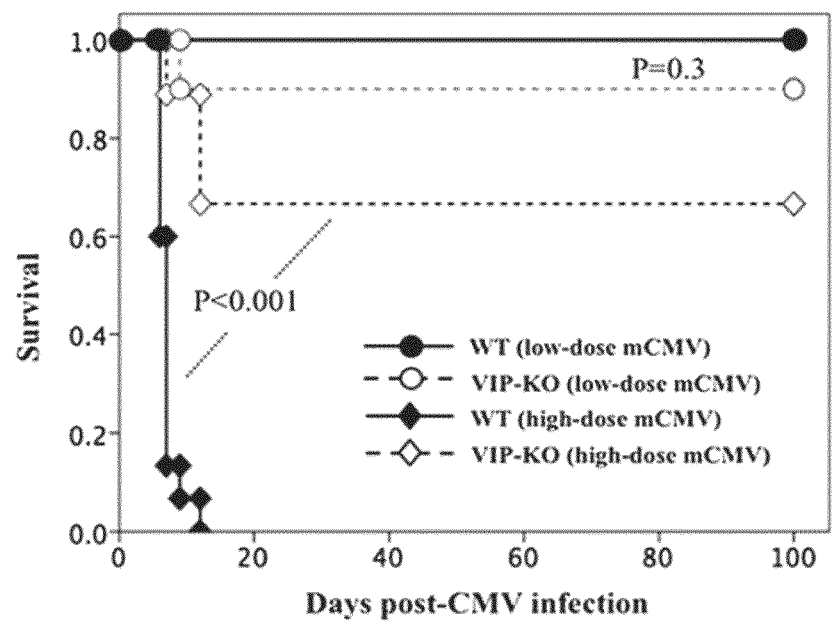
FIG. 2A shows data on survival of WT and VIP-KO mice that received graded doses of $5\times10^4$, or $1\times10^5$ PFU mCMV. VIP-KO and WT mice were infected (day 0) with low dose $5\times10^4$ PFU or high dose $1\times10^5$ PFU mCMV. Survival was recorded every day and body weight was recorded twice weekly. Peripheral blood and spleen were collected baseline, prior to mCMV infection, and 3, 7, 10, 14 and 17 days post-infection. Blood cells and splenocytes were stained with fluorescently conjugated monoclonal antibodies to CD45.2, CD3, CD4, and CD8 and analyzed by flow cytometry, and absolute numbers of cells per mL blood or per spleen were calculated.
Figure 2B:
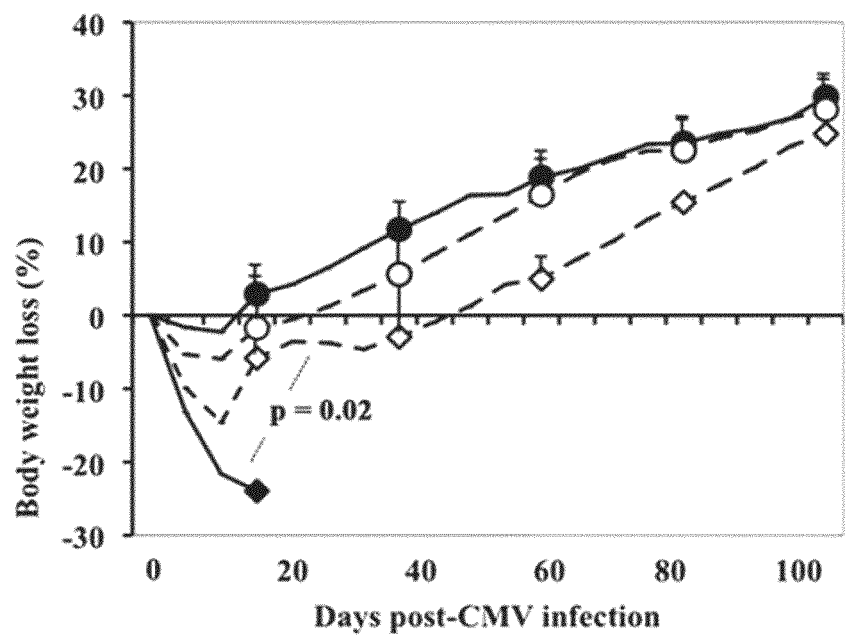
FIG. 2B shows body weight change of WT and VIP-KO mice that received graded doses of $5\times10^4$, or $1\times10^5$ PFU mCMV.
Figure 2C:
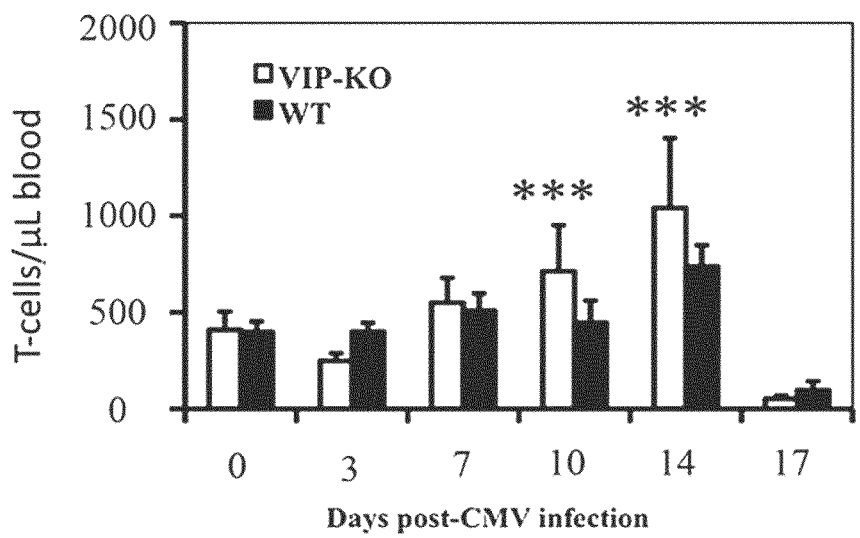
FIG. 2C shows data for total numbers of CD4$^+$ T-cells in blood following low dose mCMV infection.
Figure 2D:
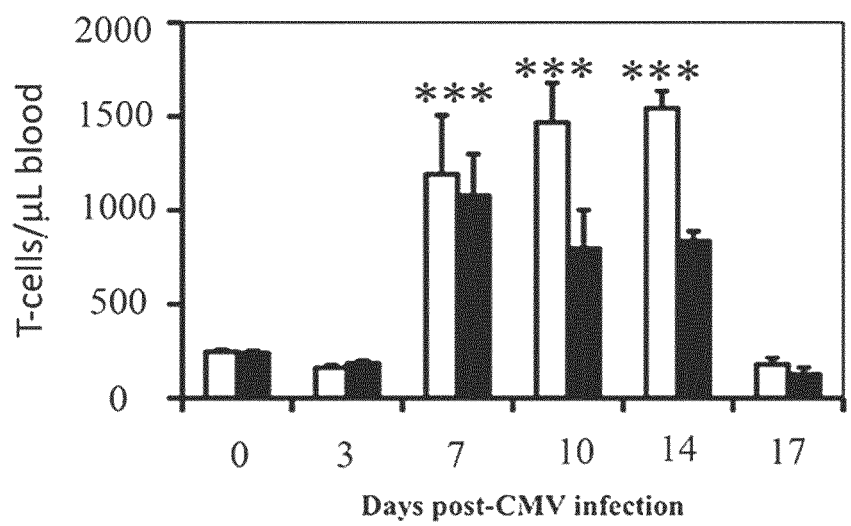
FIG. 2D shows data for total numbers of CD8$^+$ T-cells in blood following low dose mCMV infection.
Figure 2E:
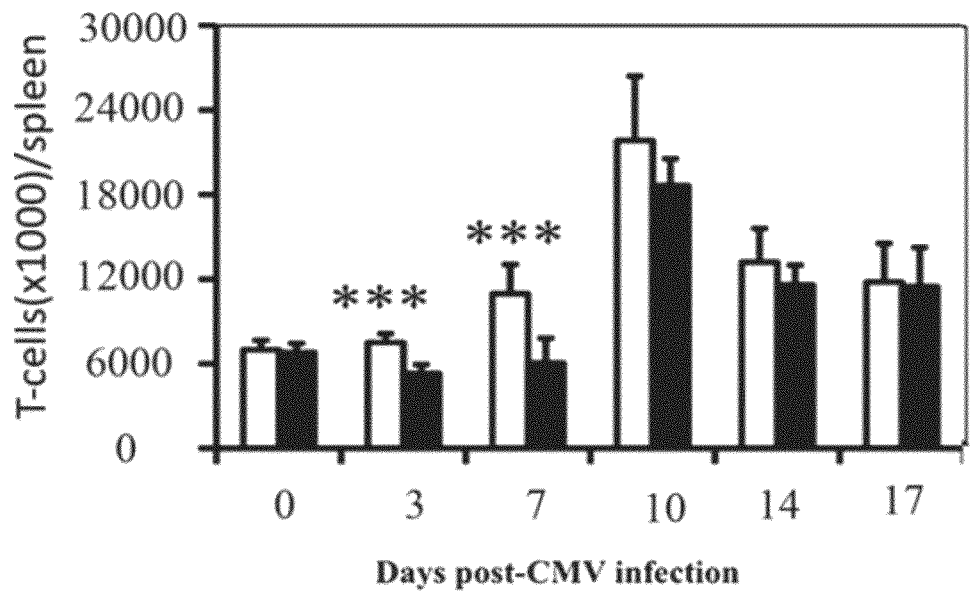
FIG. 2E shows data for total numbers of CD4$^+$ T-cells in the spleen following low dose mCMV infection.
Figure 2F:
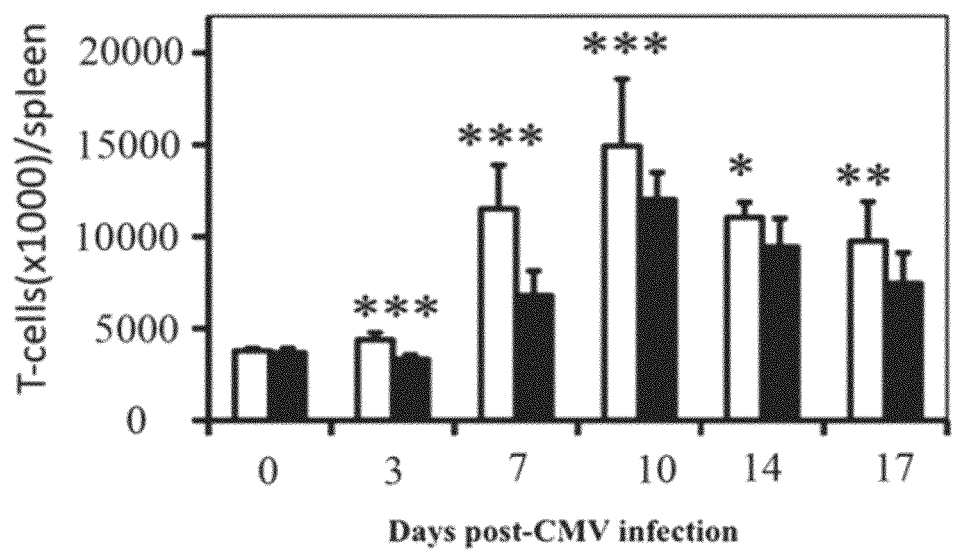
FIG. 2F shows data for total numbers of CD8$^+$ T-cells in the spleen following low dose mCMV infection.

It has been discovered that interference with VIP-signaling enhances immune responses. The role of physiological levels of VIP on immune responses to murine cytomegalovirus (mCMV) was tested using VIP-knockout (VIP-KO) mice and radiation chimeras engrafted with syngenic VIP-KO hematopoietic cells. VIP-KO mice had less weight loss and better survival following mCMV infection compared with wild-type littermates (WT). MCMV-infected VIP-KO mice had lower viral loads, faster clearance of virus, with increased numbers of IFN-γ$^+$ NK and NKT cells, and enhanced cytolytic activity of NK cells. Adaptive anti-viral cellular immunity was increased in mCMV-infected VIP-KO mice compared with WT mice, with more Th1/Tc1 polarized T-cells, fewer IL-10$^+$ T-cells, and more CMV-peptide-MHC class Metramer$^+$ CD8$^+$ T-cells. MCMV-immune VIP-KO mice had enhanced ability to clear mCMV-peptide pulsed target cells in vivo. Enhanced anti-viral immunity was also seen in WT transplant recipients engrafted with VIP-KO hematopoietic cells, indicating that VIP synthesized by neuronal cells did not suppress immune responses. Following mCMV infection there was a marked up-regulation of MHC class II and CD80 co-stimulatory molecule expression on DC from VIP-KO mice compared with DC from WT mice, while PD-1 and PD-L1 expression were up-regulated in activated CD8$^+$ T-cells and DC, respectively, in WT mice but not in VIP-KO mice. Since the absence of VIP in immune cells increased innate and adaptive anti-viral immunity by altering co-stimulatory and co-inhibitory pathways, selective targeting of VIP-signaling represents an attractive therapeutic target to enhance anti-viral immunity.

Absence of Vasoactive Intestinal Peptide Expression in Hematopoietic Cells Enhances Th1 Polarization and Anti-Viral Immunity in Mice The immuno-regulatory effect of VIP in immune responses to mCMV infection we explored. Data obtained using VIP-KO mice suggests that the absence of physiological levels of VIP in hematopoietic cells leads to striking enhancement of innate and adaptive anti-viral cellular immune responses. VIP-KO mice had less mortality and faster viral clearance compared with WT mice. The increased expansion of mCMV-peptide-MHC class I tetramer$^+$ T-cells and increased cytolytic activity of NK cells seen in VIP-KO mice are likely responsible for their greater resistance to mCMV infection. While we used the M45 epitope peptide to measure mCMV specific T-cells, and T-cells recognizing this epitope have been shown to be relative ineffective in clearing virus infected cells due to m152/gp40-mediated immune interference, the enhanced killing of M45 epitope-containing peptide-pulsed-target cells supports the contribution of M45 reactive T-cells to functional anti-viral cytotoxic activity in vivo.

To clarify the effect of various physiological sources of VIP (hematopoietic versus neuronal), C57BL/6 radiation chimeras engrafted with syngeneic VIP-KO or WT hematopoietic cells were used following myeloablative radiation. Recipients of VIP-KO hematopoietic grafts showed accelerated kinetics of cellular immune responses to primary mCMV infection and LmCMV vaccination as well as greater amnestic responses following Lm-mCMV vaccination and mCMV infection compared with recipients of wild-type grafts. These data indicate that VIP produced by hematopoietic cells has a dominant negative effect on anti-viral cellular immune responses, and that VIP synthesis by non-hematopoietic neuronal cells does not significantly affect anti-viral immune responses in this system.

Immune cells in VIP-KO mice had more Th1 polarization, less Th2 polarization, and higher MHC-II expression than those of WT mice following mCMV infection, consistent with the idea that VIP is a negative regulator of Th1 immune responses. An in vitro model of T-cells co-cultured with mCMV-peptide pulsed DC recapitulated the in vivo immunology of VIP KO mice. Co-cultures of DC and T-cells from VIP-KO mice had higher levels of IFN-γ$^+$ CD4$^-$ and CD8$^+$ T-cells and more antigen-specific anti-viral CD8$^+$ T cells compared with cultures of WT DC and WT T-cells. Conditioned media from cultures of WT T-cells and WT DC had higher levels of IL-10, and lower levels of IFN-γ, compared with culture media from VIP-KO T-cells VIP-KO DC, consistent with other reports. Heterogeneous co-cultures of VIP-KO DC and WT T-cells had the same (lower) numbers of antigen-specific anti-viral CD8$^+$ T cells as cultures of WT DC and WT T-cells, confirming that T-cells making VIP are sufficient to polarize Th2 immunity and suppress Th1 immunity, and that VIP made by T-cells is a dominant negative regulator of anti-viral immune responses.

Although it is not intended that certain embodiments be limited by any particular mechanism, it is believed that the mechanisms for the enhanced antiviral cellular immunity and greater Th1/TC1 immune polarization seen in VIP-KO mice following mCMV infection appears to be due to a profound shift in the pattern of co-stimulatory and co-inhibitory molecule expression on DC and CD8$^+$ T-cells. The higher levels of MHC-II and CD80 on cultured VIP-KO DC compared with WT DC are consistent with previous reports that mature DC activate Th1 immune responses and that supra-physiological levels of VIP induces tolerogenic DC that express lower levels of co-stimulatory molecules. Another possible mechanism is that VIP-signaling interferes with the ability of the mCMV protein m138 to target CD80 expression on DC.

An important finding is that VIP modulates the expression of the PD-1 and PD-L1 co-inhibitory molecules that regulate immune polarization and survival of T-cells. PD-L1-PD-1 interactions are known to regulate the initial priming of naive T cells by mCMV-infected APC, and are distinct from the role that PD-1 signaling plays in T cell "exhaustion" described for several persistent/chronic viral infections in humans and mice, including human CMV. Following viral infection, up-regulation of the PD-L1/L2-PD-1 pathway has been associated with immunosuppression due to cell-cycle arrest, and death of T-cells, either through the direct engagement of a death pathway or indirectly by down-regulating survival signals and growth factors. PD-L1/L2 expression on DC is associated with reduced expression of CD40, CD80, and CD86 and increased IL-10 production. DC from mice transplanted with VIP-KO cells had dramatically reduced PD-L1 expression on DC and PD-1 expression on activated memory CD8$^+$ T-cells that were associated with increased quantitative and qualitative antiviral T cell responses following mCMV infection. Physiological levels of VIP contribute to the up-regulation of PD-L1/PD-1 expression seen in WT mice following mCMV infection. The data suggests that induction of VIP is part of the active suppression of adaptive immune responses that occurs following mCMV infection.

Vaccines

In certain embodiments, the disclosure relates to vaccine compositions comprising VIP and methods of administering VIP antagonist in combination with a vaccine. A vaccine typically contains an antigen from a pathogen, and is often presented to the immune system from weakened or killed forms of the microbe or its toxins. The antigen stimulates the immune system. Vaccines may be prophylactic (e.g. to prevent or ameliorate the effects of a future infection by any pathogen), or therapeutic by being administered after infection or diagnosis of the disease.

Some vaccines contain killed, but previously virulent, micro-organisms that have been destroyed with chemicals or heat. The influenza vaccine, cholera vaccine, bubonic plague vaccine, polio vaccine, hepatitis A vaccine, and rabies vaccine are examples of a killed vaccine that are contemplated by this disclosure.

Some vaccines contain live, attenuated microorganisms. Typically these are live viruses that have been cultivated under conditions that disable certain virulent properties, or which use closely-related but less dangerous organisms to produce a broad immune response; however, some are bacterial in nature.

In certain embodiments, the vaccine is a protein subunit. Rather than introducing an inactivated or attenuated micro-organism to an immune system, a fragment of it can be used to create an immune response. Examples include the subunit vaccine against Hepatitis B virus that is composed of only the surface proteins of the virus, the virus-like particle (VLP) vaccine against human papillomavirus (HPV) that is composed of the viral major capsid protein, and the hemagglutinin and neuraminidase subunits of the influenza virus.

In certain embodiments, the vaccine comprises a polysaccharide. Certain bacteria have polysaccharide outer coats that are typically immunogenic. By linking these polysaccharides to proteins (e.g. toxins), the immune system can be led to recognize the polysaccharide as if it were a protein antigen.

Toxoid vaccines are made from inactivated toxic compounds. Examples of toxoid-based vaccines include diphtheria and tetanus toxoid. In certain embodiments, the VIP antagonist is administered in combination with DPT. DPT (also DTP and DTwP) refers to a class of combination vaccines against three infectious diseases in humans: diphtheria, pertussis (whooping cough) and tetanus. The vaccine components include diphtheria and tetanus toxoids, and killed whole cells of the organism that causes pertussis (wP). DTaP (also known as Tdap, DTPa, and TDaP) refers to similar combination vaccines in which the pertussis component is acellular. Also contemplated is the DT or TD vaccine, which lacks the pertussis component.

Other specific vaccines contemplated by the disclosure include the anthrax vaccine, e.g., culture filtrates of an avirulent, nonencapsulated strain known as V770-NP1-R, Bacille Calmette-Guérin (BCG), e.g., a strain of the attenuated live bovine tuberculosis bacillus, *Haemophilus influenzae* type B vaccine, e.g., Hib polysaccharide-protein conjugate vaccine, hepatitis A vaccine, e.g., inactivated Hepatitis A virus, hepatitis B vaccine, e.g., hepatitis B surface antigen, human papillomavirus (HPV) vaccine, e.g., non-infectious virus-like particles assembled from the L1 proteins of HPV types 6, 11, 16 and 18, meningococcal vaccine, e.g., capsular polysaccharide antigens of Neisseria meningitides serogroups A, C, Y, and W-135 strains individually conjugated to diphtheria toxoid protein.

Some cancers are caused by viruses, and traditional vaccines against those viruses, such as HPV vaccine and Hepatitis B vaccine, will prevent those cancers. It is contemplated that VIP antagonist can be administered in combination with these vaccines to improve treatment efficacy.

It is believe that cancer cells arise and are destroyed by the immune system, and that cancer forms when the immune system fails to destroy them. One approach to cancer vaccination is to separate proteins from cancer cells and immunize cancer patients against those proteins, stimulating an immune reaction that kills the cancer cells. Cancer vaccines are contemplated for the treatment of breast, lung, colon, skin, kidney, prostate, and other cancers. In certain embodiments, the disclosure relates to treating cancers by administering VIP antagonist in combination with cancer antigens.

Nucleic acid vaccines, typically a DNA plasmid, are genetically engineered to encode and/or produce one or more antigens from a pathogen. The nucleic acid is transplanted or infects host cells where the inner machinery of the cells expresses the proteins. Because these proteins are recognized as foreign, when they are processed by the host cells and displayed on their surface immune response is triggered. Cytotoxic T lymphocytes responses can also be enhanced by co-inoculation with co-stimulatory molecules such as GM-CSF, B7-1, or B7-2. In certain embodiments, a VIP antagonist may be administered in combination with nucleic acid vaccines or other co-stimulatory molecules.

In certain embodiments, the disclosure relates to methods of treating or preventing cancer comprising administering a VIP antagonist in combination with a cancer vaccine such as antigen-presenting cells comprising a cancer antigen. For example, a course of Sipuleucel-T (Provenge) treatment comprises the following steps: white blood cells from a subject, primarily antigen-presenting cells (APCs), dendritic cells, are extracted in a leukapheresis procedure. The blood product is incubated with a fusion protein (PA2024) comprising the cancer antigen prostatic acid phosphatase (PAP), which is present in many prostate cancer cells, and an immune signaling factor granulocyte-macrophage colony stimulating factor (GM-CSF) that helps the APCs to mature. The activated blood product (APC8015) is re-infused into the subject to cause an immune response against cancer cells carrying the PAP antigen. See e.g., Kantoff et al., N Engl J Med 2010, 363:411-422 hereby incorporated by reference. In certain embodiments, the disclosure relates to methods of treating prostate cancer comprising administering a VIP antagonist in combination with a peripheral-blood mononuclear cell, including antigen-presenting cells that have been activated with a recombinant protein comprising prostatic acid phosphatase and greanulocyte colony-stimulating factor.

Immunotherapies

It is contemplated that VIP antagonist may be administered to subjects before, during, or after a cell based immunotherapy including the recipient or donor. The immunotherapy may be performed in combinations with chemotherapy and/or a radiation therapy. It is contemplated that VIP antagonist may be used in combination with other immune stimulators including, but not limited to, CpG oligonucleotides, granulocyte colony stimulating factor, granulocyte-macrophage colony stimulating factor, interferon alpha, pegylated interferon, interleukin-12, interleukin-2, and pegfilgrastim.

Certain cellular immunotherapies are effective for treating cancer such as lymphocyte infusions or allogeneic bone marrow transplantations. Donor immune cells, particularly NK cells and T-cells, cells have anti-cancer cytotoxic activity. VIP antagonism enhances cellular immune responses in vivo. VIP antagonism increases the cytotoxic activity of antigen-specific T-cells and NK cells. VIP antagonism is predicted to increase the anti-cancer activity of NK cells or antigen-specific T-cells. VIP antagonism in conjunction with cellular immunotherapy is predicted to increase the efficacy of said therapy. It is believed that the absence of VIP does not increase the "off-target" graft versus host disease activity of donor lymphocytes in recipients of allogeneic bone marrow transplantation. Thus, administration of VIP antagonists to subjects with cancer receiving cellular therapies, e.g., donor lymphocyte infusions or allogeneic bone marrow transplantation, will increase the anti-cancer activity of said therapy.

In certain embodiments, the disclosure relates to methods of treating cancer by performing a stem cell transplantation comprising administering a VIP antagonist to the subject in combination with transplanting a multipotent hematopoietic stem cell derived from the subject (self) or a donor. The stem cells may be collected from peripheral blood such as cord blood or placenta-derived stem cells or from the bone marrow. To limit the risks of transplanted stem cell rejection or of severe graft-versus-host disease, the donor will typically have the substantially human leukocyte antigens (HLA) as the recipient; however the donor may have mismatches for certain antigens.

In certain embodiments, the disclosure relates to lymphocyte infusions after a hematopoietic progenitor cell transplant to treat a hematologic malignancy (e.g., cancer of the blood or bone marrow, such as leukemia or lymphoma). A transplant recipient is typically infused with lymphocytes obtained in a leukapheresis procedure from the original allogeneic stem cell (hematopoietic progenitor cell) donor.

In certain embodiments, the disclosure relates to extraction of lymphocytes from the blood and expanding in vitro against tumor antigen(s) and optionally exposing the cells with an appropriate stimulatory cytokine and/or a VIP antagonist.

In certain embodiments, the disclosure relates to methods of enhancing topical immunotherapies comprising administering a VIP antagonist in combination with providing an immune enhancement cream, such as imiquimod, comprising an interferon producing drug, that causes the activation of T-cells.

In certain embodiments, it is contemplated that VIP antagonists can be used in combination with adoptive cell therapies. For example, T cells with a naturally occurring reactivity to cancer can be found infiltrated in tumors of the subject. The tumor can be harvested, and these tumor-infiltrating lymphocytes (TIL) can be expanded, or made more effective, in vitro using interleukin-2 (IL-2), anti-CD3 and allo-reactive feeders. These T cells can then be transferred back into the subject along with administration of a VIP antagonist. Before reinfusion, lymphodepletion of the recipient is typically done to eliminate regulatory T cells as well as normal endogenous lymphocytes that compete with the transferred cells. It is also contemplated that the adoptive cell transfer of lymphocytes may be transduced with a vector encoding T cell receptors (TCRs) that recognize a cancer antigen.

Terms

The terms "vasoactive intestinal peptide" and "VIP" refer to (SEQ ID NO:3) HSDAVFTDNYTRLRKQMAVKKYLNSILN unless the context suggests otherwise. VIP is a multifunctional endogenous polypeptide that modulates both innate and adaptive immunity at multiple levels of immune cell differentiation and activation. There are two human isoforms of the preproprotein: human isoform 1 (SEQ ID NO:1) 1 MDTRNKAQLL VLLTLLSVLF SQTSAWPLYR APSALRLGDR IPFEGANEPD QVSLKEDIDM 61 LQNALAENDT PYYDVSRNAR HADGVFTSDF SKLLGQLSAK KYLESLMGKR VSSNISEDPV 121 PVKRHSDAVF TDNYTRLRKQ MAVKKYLNSI LNGKRSSEGE SPDFPEELEK and human isoform 2 (SEQ ID NO:2) 1 MDTRNKAQLL VLLTLLSVLF SQTSAWPLYR APSALRLGDR IPFEGANEPD QVSLKEDIDM 61 LQNALAENDT PYYDVSRNAR HADGVFTSDF SKLLGQLSAK KYLESLMGKR VSNISEDPVP 121 VKRHSDAVFT DNYTRLRKQM AVKKYLNSIL NGKRSSEGES PDFPEELEK.

VIP is typically secreted by a variety of cells such as neurons (in both the central and peripheral nervous systems) B-cells, T-cells, and accessory cells. VIP and the closely related neuropeptide pituitary adenylyl cyclase-activating polypeptide (PACAP) bind to three known receptors- VPAC1, VPAC2, and PAC1. It is believed that T-cells and dendritic cells (DC) express VPAC1 and VPAC2, but not PAC1. PAC1 is mainly expressed on neuron and endocrine cells in the brain and pituitary and adrenal glands, and in most forms selectively binds PACAP.

In adaptive immune responses, VIP polarizes $CD4^+$ T-cells to an immunosuppressive Th2 response while suppressing the Th1 responses. T-cell activation and differentiation induce VPAC2 expression, while VPAC1 is down-regulated following stimulation of human blood T-cells with anti-CD3 monoclonal antibody plus PMA. VIP also acts on APC and regulates their function. Through the VPAC1 receptor, VIP leads to the development of bone marrow-derived tolerogenic DCs in vitro and in vivo. In a mouse model of bone marrow transplantation, DC that were differentiated in the presence of VIP, and then transplanted along with bone marrow cells and splenic T-cells induced the generation of regulatory T-cells and protected mice from acute graft versus host disease (GvHD). Th2 polarization is achieved partly through VIP regulation of costimulatory signals on antigen presenting cells (APC) and inhibition of IL-1, TNF-α, IL-6, and IL-12 production. VIP suppresses expression of the pattern recognition receptors toll-like receptor (TLR) 2 and TLR4 on APC and inhibits TLR3-signaling. Conversely, binding of ligands to TLR2, TLR4, and TLR7 down-regulate VPAC2 expression on APC.

The term "VIP antagonist" refers to any molecule that inhibits or detracts from the ability of VIP to alter immune responses. VIP antagonists are known including VIP analogues, VIP fragments, growth hormone-releasing factor analogs and hybrid peptides. A number of VIP antagonists are disclosed in U.S. Pat. Nos. 5,565,424; 7,094,755; 6,828,304, and are all hereby incorporated by reference. Some examples of VIP antagonist include [Ac-Tyr1,D-Phe2]GRF 1-29, amide, i.e., (SEQ ID NO:4) YFDAIFTNSYRKVLGQLSARKLLQDIMSR (Modifications: Tyr-1=N-terminal Ac, Phe-2=D-Phe, Arg-29=C-terminal amide); VIP (6-28), i.e., (SEQ ID NO:5) FTDNYTRLRKQMAVKKYLNSILN (Modifications: Asn-23=C-terminal amide); [D-p-Cl-Phe6, Leu17]-VIP, i.e., (SEQ ID NO:6) HSDAVFTDNYTRLRKQLAVKKYLN-SILN (Modifications: Phe-6=p-Cl-D-Phe, Asn=C-terminal amide); VIP-hyb also known as VIPhybrid, i.e., a hybrid peptide of neurotensin and VIP consisting of an N-terminal (SEQ ID NO:7) KPRRPY, also designated neurotensin (6-11)] followed by the C-terminal 22 amino acids of VIP, i.e., (SEQ ID NO:8) TDNYTRLRKQMAVKKYLNSILN, also designated VIP (7-28); N-terminal Stearyl, Norleucine 17 VIPhyb, i.e., (SEQ ID NO: 9) KPRRPY-TDNYTRLRKQXAVKKYLNSILN, wherein St is Stearyl and X is norleucine; Ac His1 [D-Phe(2), Lys(15), Arg(16), Leu(27)]-VIP(1-7)/GRF(8-27), i.e., (SEQ ID NO:10) HFDAVFTNSYRKVLKRLSARKLLQDIL, C-terminal amide; and pituitary adenylate cyclase-activating polypeptide, PACAP (6-38) C-terminal amide, i.e., (SEQ ID NO:11) TDSYSRYRKQMAVKKYLAAVLGKRYKQRVKNK. It is contemplated that any of these molecules may be modified with hydrocarbon or polyethylene glycol groups in order to provide improve properties such as solubility, bioavailability, and/or biological degradation.

An amount sufficient" or "an effective amount" is that amount of a given VIP antagonist which antagonizes or inhibits the VIP-associated activity of interest or, which provides either a subjective relief of a symptom(s) or an objectively identifiable improvement as noted by the clinician or other qualified observer. The dosing range varies with the VIP antagonist used, the VIP-associated activity to be antagonized, the route of administration and the potency of the particular antagonist.

In therapeutic applications, the VIP antagonists of the invention are administered to a patient in an amount sufficient to antagonize (i.e., inhibit) VIP-associated activity. An amount adequate to accomplish this is defined as "therapeutically effective dose." Amounts effective for this use will depend on, for example, the particular VIP antagonist emploYed, the VIP-associated activity to be inhibited or antagonized, the manner of administration, the weight and general state of health of the patient, and the judgment of the prescribing physician. For example, for inhibition of tumor growth (e.g., MIX or neuroblastoma), an amount of VIP antagonist falling within the range of 0.35 µg to 3.5 µg per 100 g tumor, injected directlY into the solid tumor would be a therapeutically effective amount. For inhibition of circadian rhythm, an amount of VIP antagonist falling within the range of a 1 to 10 mg dose given intranasally once a day (in the evening) would be a therapeutically effective amount.

Antibodies

The disclosure also includes relates to a VIP antagonist antibody that specifically binds VIP or VIP receptor such as VPAC1, VPAC2, and PAC1. The disclosure should not be construed as being limited solely one type of antibody. Rather, should be construed to include antibodies that specifically bind VIP, VIP preproproteins, VIP receptors, or portions thereof. One skilled in the art would appreciate, based upon the disclosure provided herein, that the antibody can specifically bind with any portion of the polypeptide and the polypeptide can be used to generate antibodies specific. However, in certain embodiments, the disclosure is not limited to using the full-length polypeptide corresponding to VIP.

The antibodies can be produced by immunizing an animal such as, but not limited to, a rabbit or a mouse, with a protein, or a portion thereof, or by immunizing an animal using a protein comprising at least a portion of the polypeptide corresponding to VIP. One skilled in the art would appreciate, based upon the disclosure provided herein, smaller fragments of these proteins can also be used to produce antibodies that specifically bind the polypeptide.

Certain embodiments of the disclosure encompass polyclonal, monoclonal, synthetic antibodies, and the like. Moreover, the antibody can be used to detect and or measure the amount of protein present in a biological sample using well-known methods such as, but not limited to, Western blotting and enzyme-linked immunosorbent assay (ELISA). The antibody can also be used to immunoprecipitate and/or immuno-affinity purify their cognate antigen using methods well-known in the art. Thus, by administering the antibody to a cell or to the tissue of an animal, or to the animal itself, the interactions between VIP and its cognate receptor are therefore inhibited.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See, e.g., U.S. Pat. Nos. 4,816,567 and 4,816,397. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An VIP antibody or antibody fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MEW Class II; these peptides represent potential T-cell epitopes. For detection of potential T-cell epitopes, a computer modeling approach termed "peptide threading" can be applied, and in addition a database of human MEW class II binding peptides can be searched for motifs present in the VH and VL sequences. These motifs bind to any of the 18 major MEW class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Cytomegalovirus (CMV)

CMV belongs to the beta-herpesvirinae subfamily of Herpesviridae. In humans it is commonly known as HCMV or Human Herpesvirus 5 (HHV-5). Herpesviruses typically share a characteristic ability to remain latent within the body over long periods. HCMV infection may be life threatening for patients who are immunocompromised. In certain embodiments, the disclosure relates to methods of treating a subject diagnosed with cytomegalovirus or preventing a cytomegalovirus infection by administration of a VIP antagonist. In certain embodiments, the subject is immunocompromised. In typical embodiments, the subject is an organ transplant recipient, undergoing hemodialysis, diagnosed with cancer, receiving an immunosuppressive drug, and/or diagnosed with an HIV-infection. In certain embodiments, the subject may be diagnosed with cytomegalovirus hepatitis, the cause of fulminant liver failure, cytomegalovirus retinitis (inflammation of the retina, may be detected by ophthalmoscopy), cytomegalovirus colitis (inflammation of the large bowel), cytomegalovirus pneumonitis, cytomegalovirus esophagitis, cytomegalovirus mononucleosis, polyradiculopathy, transverse myelitis, and subacute encephalitis. In certain embodiments, VIP antagonist is administered in combination with an antiviral agent such as valganciclovir or ganciclovir. In certain embodiments, the subject undergoes regular serological monitoring.

HCMV infections of a pregnant subject may lead to congenital abnormalities. Congenital HCMV infection occurs when the mother suffers a primary infection (or reactivation) during pregnancy. In certain embodiments, the disclosure relates to methods of treating a pregnant subject diagnosed with cytomegalovirus or preventing a cytomegalovirus infection in a subject at risk for, attempting to become, or currently pregnant by administering a VIP antagonist.

Subjects who have been infected with CMV typically develop antibodies to the virus. A number of laboratory tests that detect these antibodies to CMV have been developed. The virus may be cultured from specimens obtained from urine, throat swabs, bronchial lavages and tissue samples to detect active infection. One may monitor the viral load of CMV-infected subjects using PCR. CMV pp65 antigenemia test is an immunoaffinity based assay for identifying the pp65 protein of cytomegalovirus in peripheral blood leukocytes. CMV should be suspected if a patient has symptoms of infectious mononucleosis but has negative test results for mononucleosis and Epstein-Barr virus, or if they show signs of hepatitis, but have negative test results for hepatitis A, B, and C. A virus culture can be performed at any time the subject is symptomatic. Laboratory testing for antibody to CMV can be performed to determine if a subject has already had a CMV infection.

The enzyme-linked immunosorbent assay (or ELISA) is the most commonly available serologic test for measuring antibody to CMV. The result can be used to determine if acute infection, prior infection, or passively acquired maternal antibody in an infant is present. Other tests include various fluorescence assays, indirect hemagglutination, (PCR), and latex agglutination. An ELISA technique for CMV-specific IgM is available.

Combination Therapies

In some embodiments, the disclosure relates to treating a viral infection by administering a VIP antagonist in combination with a second antiviral agent. In further embodiments, VIP antagonist is administered in combination with one or more of the following agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments, the disclosure relates to methods of treating viral infections by administering a VIP antagonist and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a VIP antagonist in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a VIP antagonist in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include Privigen, Hizentra, and WinRho. WinRho is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti-Rho(D) (anti-D)-coated RBC complexes resulting in Fc receptor blockade, thus sparing antibody-coated platelets.

In certain embodiments, it is contemplated that the vaccine may be used to treat or prevent a bacterial infection in which case an anti-bacterial agent may be administered in combination with VIP antagonist and the vaccine. Exemplary antibiotics include, but are not limited to, amikacin, gentamicin, kanamycin, neomycin, netilmicin, tobramycin, paromomycin, ansamycins, geldanamycin, herbimycin, carbacephem, loracarbef, carbapenems, ertapenem, doripenem, imipenem/cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, telavancin, lincosamides, clindamycin, lincomycin, lipopeptide, daptomycin, azithromycin, clarithromycin, dirithromycin, erythromycin, roxithromycin, troleandomycin, telithromycin, spectinomycin, monobactams, aztreonam, nitrofurans, furazolidone, nitrofurantoin, amoxicillin, ampicillin, azlocillin, carbenicillin, cloxacillin, dicloxacillin, flucloxacillin, mezlocillin, methicillin, nafcillin, pxacillin, penicillin G, penicillin V, piperacillin, temocillin, ticarcillin, penicillin combinations, amoxicillin/clavulanate, ampicillin/sulbactam, piperacillin/ tazobactam, ticarcillin/clavulanate, bacitracin, colistin, polymyxin B, quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfonamidochrysoidine (archaic), sulfacetamide, sulfadiazine, silver sulfadiazine, sulfamethizole, sulfamethoxazole, sulfanilimide (archaic), sulfasalazine, sulfisoxazole, trimethoprim, trimethoprim-sulfamethoxazole (co-trimoxazole) (TMP-SMX), demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, mupirocin, platensimycin, quinupristin/dalfopristin, rifaximin, thiamphenicol, tigecycline, or tinidazole, or combinations thereof.

EXAMPLES

Example 1

VIP-KO Mice were Resistant to mCMV Infection

The hematological and immunological phenotypes of VIP-KO mice were compared. No significant differences were found comparing blood from naïve WT and VIP-KO mice in the numbers of total leukocytes, CD4, CD8, αβ TCR T-cells, γδ T-cells, B-cells, myeloid leukocytes, and DCs in blood. VIP-KO and WT mice were infected with a non-lethal dose of mCMV ($5 \times 10^4$ pfu) and sacrificed 3, 10 and 17 days later, VIP-KO mice had significantly less virus in their liver, a target for mCMV infection, with more rapid clearance of virus than mCMV infected WT mice ($p<0.001$; FIG. 1). To test whether VIP-KO mice had better survival following mCMV infection, VIP-KO and WT mice were infected intraperitoneally with either $1 \times 10^5$ PFU/mouse (high-dose) or $5 \times 10^4$ PFU/mouse (low dose) mCMV. All WT mice given high-dose mCMV died by day 10 post-infection compared with 65% survival of the VIP-KO mice ($p<0.001$, FIG. 2A). Following low-dose mCMV infection both WT and VIP-KO mice had transient lethargy and weight-loss, with recovery to baseline values by day 20 post-infection, with 100% of WT mice and 92% of VIP-KO mice surviving to day 100 post-infection (FIG. 2). In a parallel experiment, serial measurements of CD4 and CD8 T-cells following mCMV infection showed that VIP-KO mice had more CD4$^-$ and CD8$^-$ T-cells in their blood and spleen compared with WT mice.

Example 2

Innate and Adaptive Anti-Viral Responses were Enhanced in the Absence of VIP

Figure 3A:
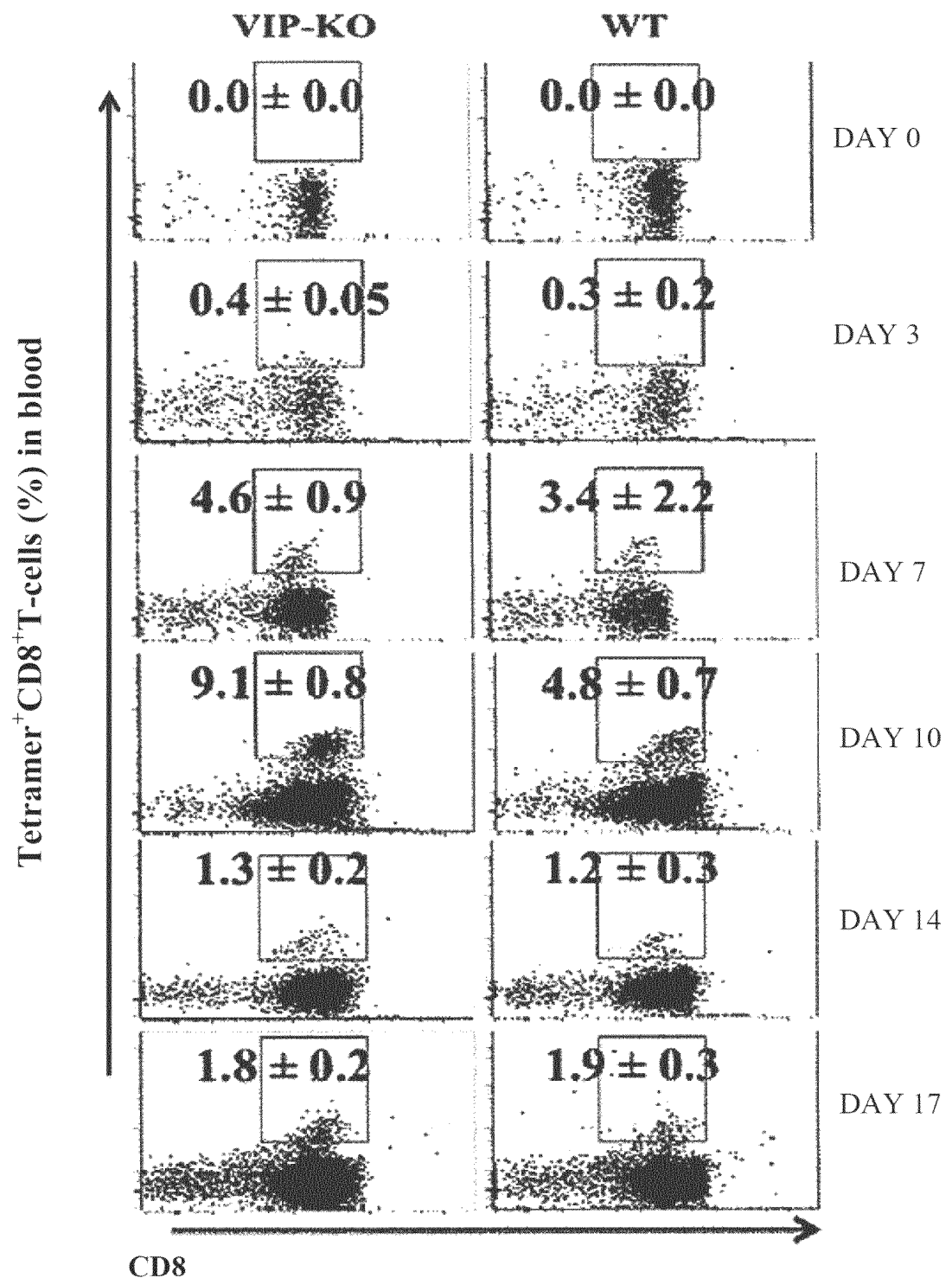
FIG. 3A shows data suggesting mice lacking VIP had larger increases of antigen-specific T-cells following mCMV infection. VIP-KO and WT mice were infected (day 0) with low dose 5×104 PFU or high dose 1×10$^5$ PFU mCMV. Peripheral blood and spleen were collected at baseline, prior to infection and 3, 7, 10, 14 and 17 days post-mCMV infection. Blood cells and splenocytes were stained with fluorescently conjugated monoclonal antibodies to CD45.2, CD3, CD4, CD8 and mCMV M45-peptide specific MHC class I tetramer reagents, analyzed by flow cytometry, and absolute numbers of cells per mL blood and per spleen were calculated. NK cell killing activity were measured by Cr51 releasing assay using YAC-1 pulsed Cr51. A. Percentages of CD8$^+$ T-cells in blood and spleen stained with the mCMV-peptide MHC class I MHC tetramer following low-dose mCMV infection.
Figure 3B:
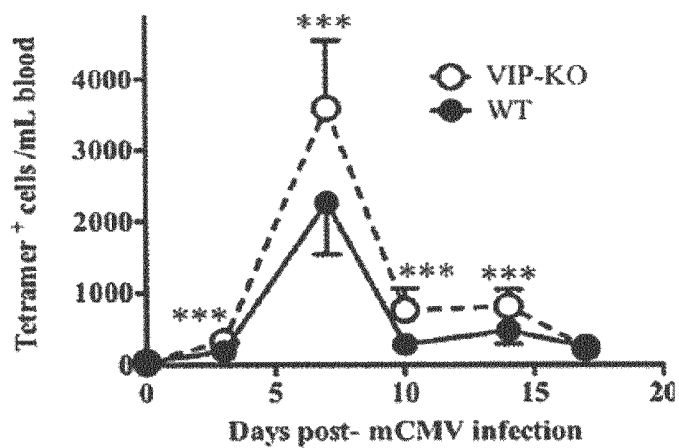
FIG. 3B shows data, absolute numbers of mCMV-peptide MHC class I MHC tetramer$^+$ CD8$^+$ T-cells/mL in blood following low-dose mCMV infection.
Figure 3C:
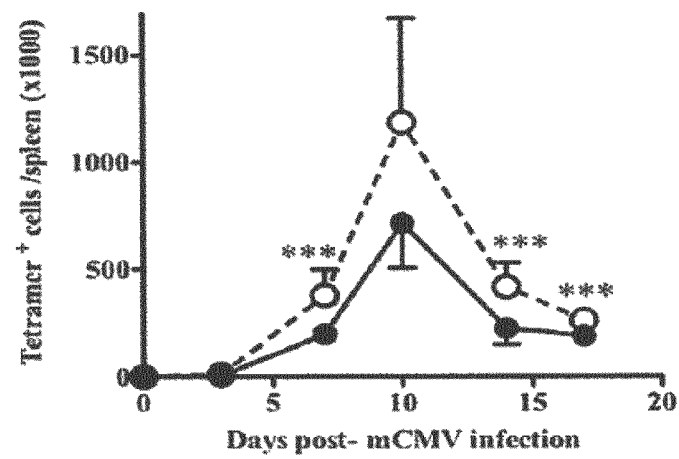
FIG. 3C shows data, absolute numbers of mCMV-peptide MHC class I MHC tetramer$^+$ CD8$^+$ T-cells in the spleen following low-dose mCMV infection.
Figure 3D:
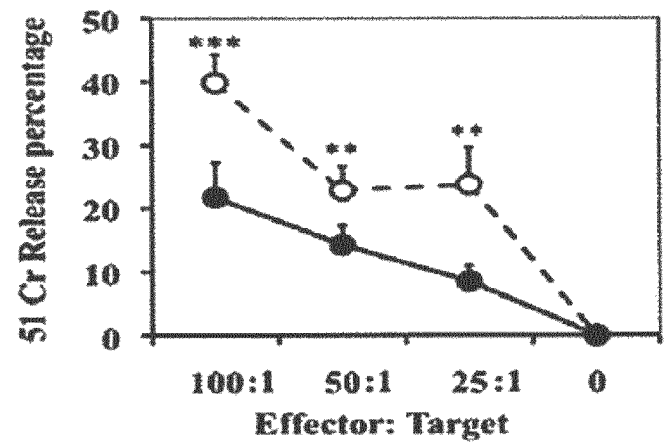
FIG. 3D shows data, NK cells mediated cytolytic activity.  Signifies p<0.01 and * signifies p<0.001, denoting a significant difference between VIP-KO and wild-type mice.
Figure 4A:
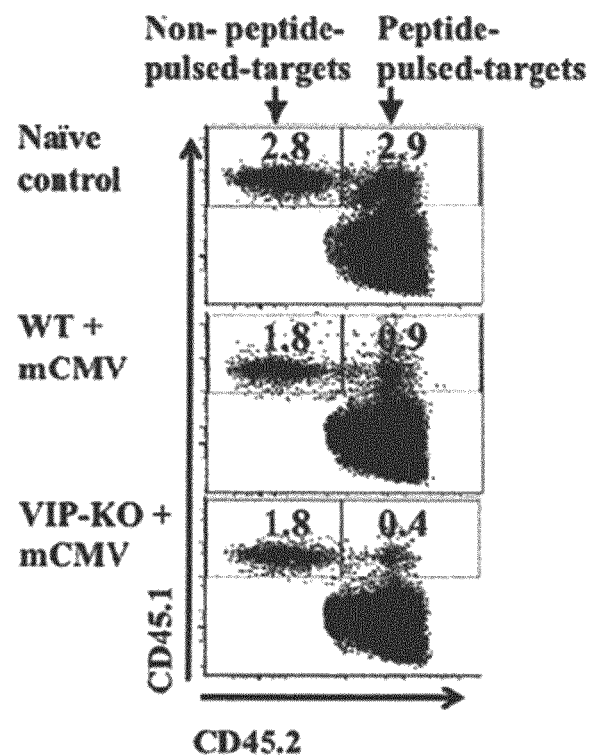
FIG. 4A shows data suggesting VIP-KO mice had increased cytolytic activity against M45 peptide-pulsed targets following mCMV infection. A mixture of peptide-pulsed targets (CD45.1$^+$ CD45.2$^+$) and non-pulsed targets (CD45.2$^-$ CD45.1$^+$) were adoptively transferred to VIP-KO and WT mice 9 days after infection with low-dose mCMV. Target cells were harvested from the recipient spleens 16 hours after iv injection, and peptide-pulsed targets and non-pulsed targets were differentiated by flow cytometry following staining for CD45 congenic markers. A. A representative flow cytometry analysis plot of splenocytes from recipient mice showing mean percentages of peptide-pulsed target cells and non-pulsed target cells
Figure 4B:
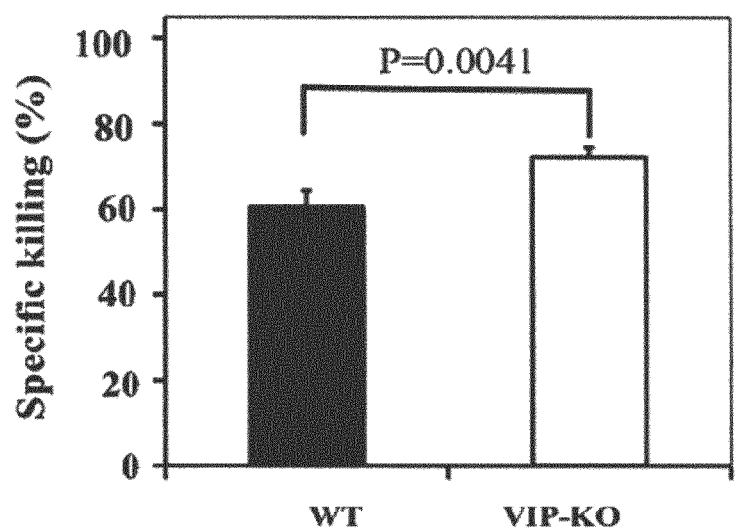
FIG. 4B shows data, calculated mean specific cytolytic activity.

VIP-KO mice had significantly higher percentages (FIG. 3A) and absolute numbers of antigen-specific mCMV peptide-MHC-class I tetramer$^+$ CD8$^-$ T-cells in the blood (FIG. 3B) and spleen (FIG. 3C) following low-dose mCMV infection than WT mice. The highest frequency of mCMV peptide-MHC-class I tetramer$^-$ CD8$^+$ T-cells in the blood was seen on day +10 post-infection with 9.1%±0.8% of blood CD8$^+$ T-cells in VIP KO mice vs. 4.8%±0.7% of blood CD8$^+$ T-cells in WT mice ($p<0.001$; FIG. 3A). Since lethality was 100% in WT mice receiving high-dose mCMV compared with 35% mortality among VIP-KO mice ($p<0.001$), a longitudinal comparison of the numbers of antigen specific T-cells in WT vs. VIP KO mice could not be performed, but analysis at day 3 showed that VIP-KO mice had greater numbers of mCMV peptide-MHC-class I tetramer$^+$ CD8$^+$ T-cells (295/mL±40/mL) compared with WT mice (124/mL±38/mL, $p<0.001$). Enhanced innate anti-viral immunity among VIP-KO mice was evidenced by higher levels of NK-mediated cytotoxicity against YAC1 targets in VIP-KO splenocytes harvested 3 days post-infection (FIG. 3D). Using mCMV-peptide-pulsed and non-pulsed congenic splenocytes as targets in an in vivo cytotoxicity assay in immune mice (previously infected with low dose mCMV), the specific lysis of mCMV-peptide-pulsed targets was significantly enhanced in VIP-KO mice compared with WT mice (FIG. 4A, B). Significantly, VIP-KO mice had similar baseline-numbers but more IFN-γ-expressing NK, NKT cells, and Th1/Tc1 polarized (IFN-γ$^+$ and TNF-α$^+$) T-cells on days 3-17 post-infection compared with WT mice.

Example 3

Figure 5A:
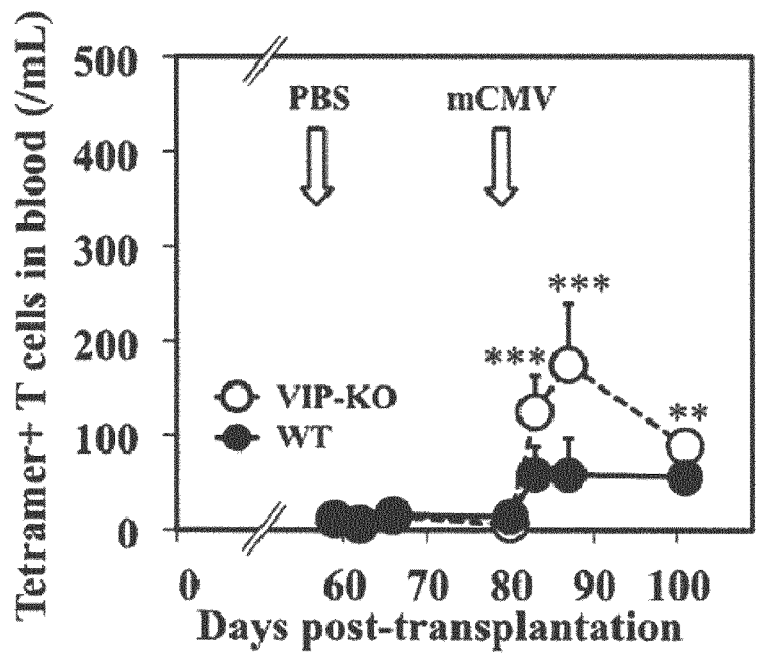
FIG. 5A shows data suggesting radiation chimeras engrafted with hematopoietic cells from VIP-KO donors had enhanced primary and secondary antigen specific cellular immune responses following Lm-mCMV vaccination and mCMV infection. Syngeneic bone marrow chimeric mice were generated by transplanting lethally irradiated H-2Kb recipients with 3×10$^3$ HSC, 5×10$^4$ DC and 3×10$^5$ T-cells from either VIP-KO or WT H-2Kb donor mice. 59 days post-transplant, mice were vaccinated with 1×10$^6$ CFU Lm-MCMV or PBS, and then 80 days post-transplant, mice were infected with low dose 5×10$^4$ PFU mCMV. Blood samples were collected at day 59, 62, 66, 80, 83, 87 and 101 post-transplantation and analyzed by flow cytometry for mCMV-peptide-MHC class I tetramer$^+$ CD8$^+$ T-cells. A. Mice were treated first with PBS then infected with mCMV.
Figure 5B:
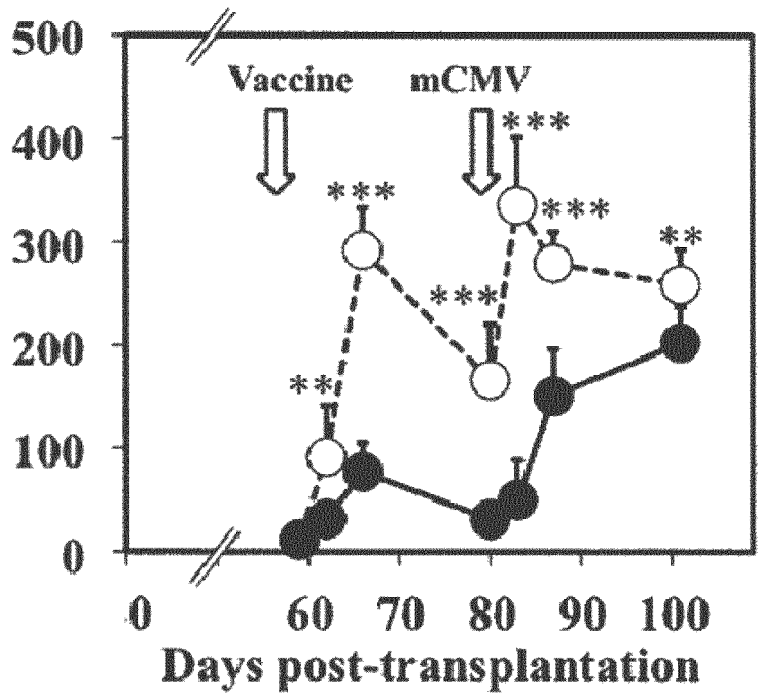
FIG. 5B shows data, primary and secondary immune responses in mice following vaccination with Lm-MCMV and then infection with low-dose mCMV. *** Signifies p<0.001 comparing tetramer$^+$ T-cell levels between mice transplanted with VIP-KO hematopoietic cells and WT hematopoietic cells.

The Absence of VIP Expression in Donor Hematopoietic Cells Enhanced Anti-Viral Immunity in Radiation Hematopoietic Chimeras Since VIP is expressed in multiple cell lineages, whether mice lacking VIP expression only in their hematopoietic cells had the same level of enhanced anti-viral immunity was tested. VIP-KO mice were used as donors of hematopoietic cells and created radiation chimeras with syngenic BMT in which recipients had >95% donor cell engraftment. The day 59 survival of mice transplanted with VIP-KO $3 \times 10^3$ FACS purified HSC, $5 \times 10^4$ FACS purified DC and $3 \times 10^5$ MACS purified T-cells (75%±10%) was similar to the survival seen among mice transplanted with WT HSC, DC and T-cells (80%±9%). To explore the effect of VIP expression in hematopoietic cells on primary and secondary immune responses, VIP-KO ◊ WT and WT ◊ WT syngeneic transplant recipients were primed with PBS or the Lm-MCMV vaccine (containing mCMV immunodominant peptide M45 aa 985~993) followed by infection 21 days later with low dose mCMV (FIG. 5A, B). Peripheral blood samples obtained prior to Lm-MCMV vaccination (day 59 post-transplant), after vaccination, and following mCMV infection (day 80 post-transplant) were analyzed for the numbers of mCMV peptide MHC class I tetramer$^+$ CD8$^+$ T-cells. Non-immunized WT and VIP-KO chimeric mice had minimal numbers of mCMV-peptide tetramer$^+$ CD8$^+$ T-cells in their blood at baseline (FIG. 5A). Following primary mCMV infection, recipients engrafted with VIP-KO hematopoietic cells had significantly more mCMV-peptide tetramer$^+$ CD8$^+$ T-cells in their blood compared with WT mice (FIG. 5A). Vaccination with Lm-MCMV led to a larger increase in blood mCMV tetramer$^+$ T-cells in the VIP-KO ◊ WT chimeras compared with WT ◊ WT chimeras (FIG. 5B) indicating that mCMV peptide presentation alone in VIP-KO mice (in the absence of viral infection) was sufficient to result in enhanced expansion of antigen-specific T-cells. Subsequent infection of the Lm-MCMV vaccinated mice with low dose mCMV led to an accelerated anamnestic response in VIP-KO ◊ WT chimeras compared with mice engrafted with WT BM (FIG. 5B).

Since both T-cells and accessory cells can secrete VIP, the role of VIP synthesis by different immune cell subsets was explored by creating radiation chimeras engrafted with the combination of donor DC & HSC from VIP-KO mice and donor T-cells from WT mice. Mice transplanted with the heterogeneous combination of VIP-KO HSC & DC and WT T-cells did not show the enhanced immune responses seen in mice engrafted with the homogeneous combination of VIP-KO HSC, DC and T-cells (FIG. 5B) indicating that VIP production by donor T-cells was sufficient to attenuate anti-viral cellular immunity.

Example 4

Figure 6A:
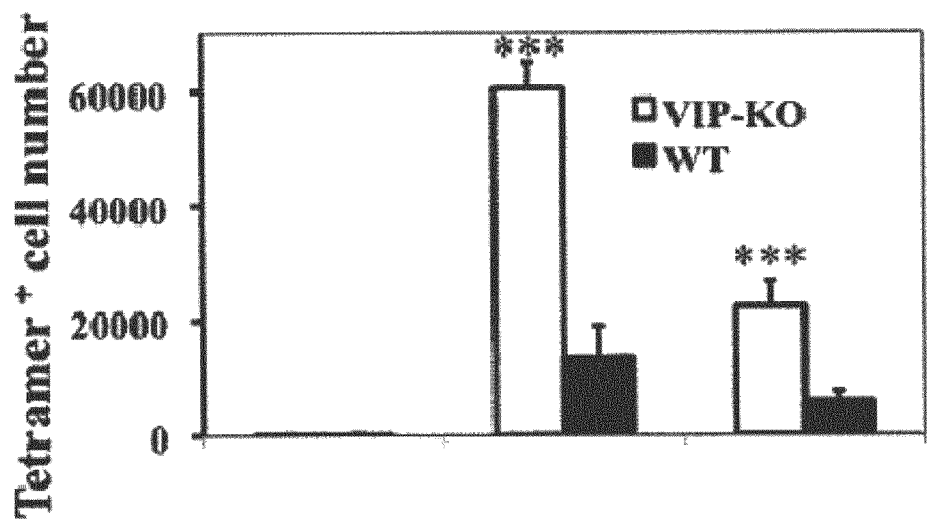
FIG. 6A shows data suggesting the generation of antigen-specific anti-viral T-cells and Th1 polarization was increased in cultures of DC and T-cells from VIP-KO mice compared with cells from WT mice. DC and T-cells were isolated from spleens of VIP-KO and WT mice, and from radiation chimeric mice that received homogeneous grafts from VIP-KO or WT (3×10$^3$) HSC, (5×10$^4$) DC and (1×10$^6$) T-cells, and heterogeneous grafts from the combination of VIP-KO HSC and DC and WT T-cells 15 days following infection with 5×10$^4$ PFU (low dose) mCMV. FACS-purified DC from these mice were incubated with 3 μM mCMV peptide for 30 minutes, washed, and then co-cultured with T-cells from the same groups. On day 3 and day 7 of culture, antigen-specific T-cells were measured by FACS using mCMV-peptide-MHC class I tetramer reagent. A and B: the absolute numbers of mCMV-peptide-MHC class I tetramer$^+$ cells per mL in cultures of cells from non-transplanted.
Figure 6B:
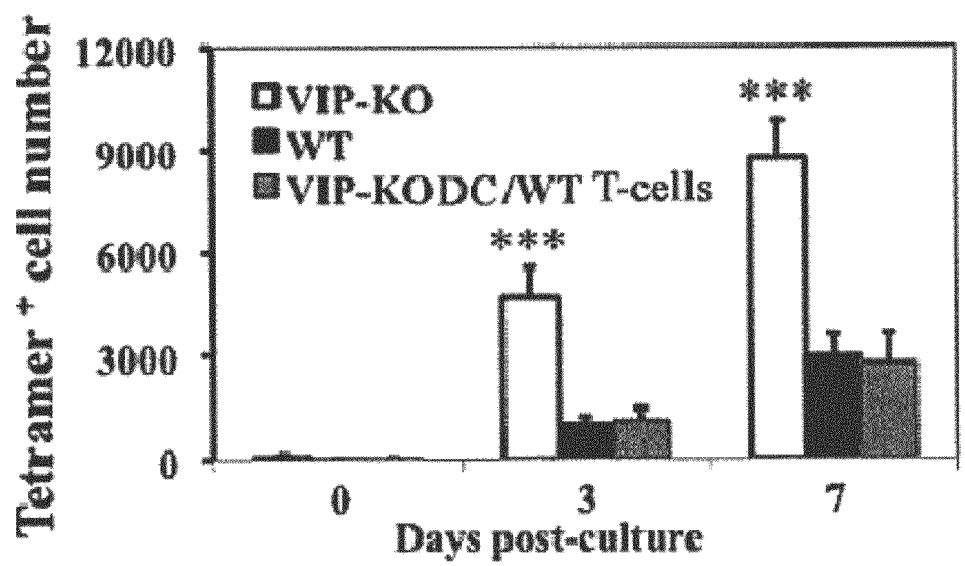
FIG. 6B shows data, radiation chimeric mice.
Figure 6C:
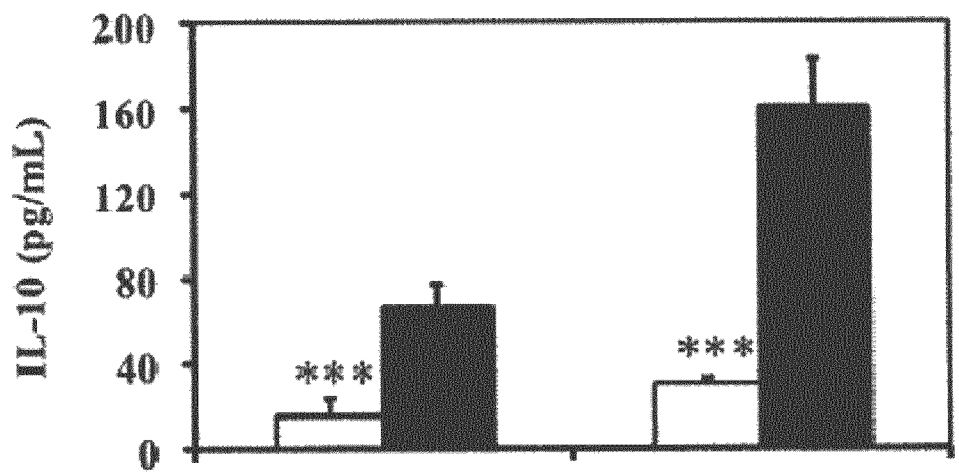
FIG. 6C shows data, day 0 data were obtained using cells from non-infected mice. Culture media from day 3 cultures of cells from radiation chimeric mice were assayed for IL-10.
Figure 6D:
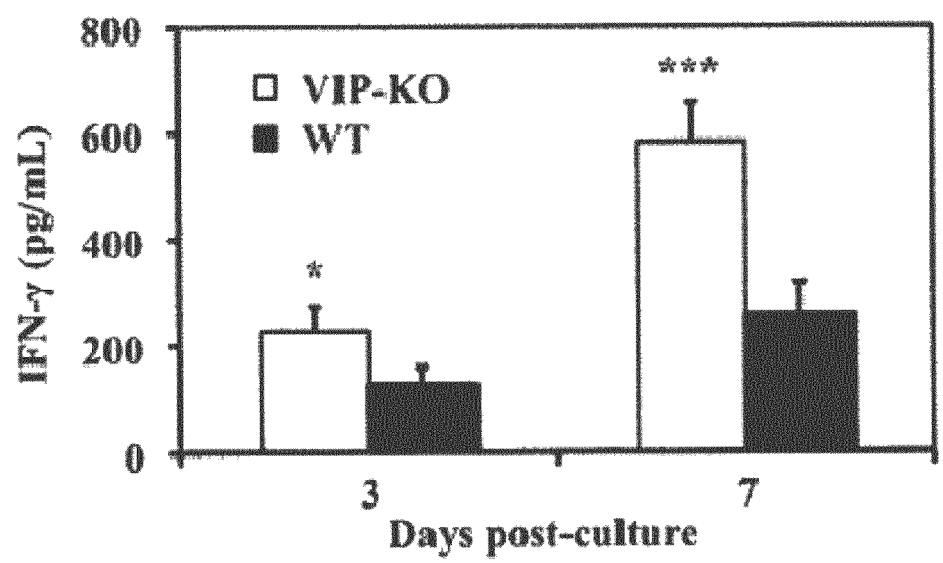
FIG. 6D shows data, IFN-γ by ELISA. * Signifies p<0.05,  p<0.01, * p<0.001 comparing VIP-KO mice and WT groups. Means±SE from pooled results of 3 repeat experiments. The experiment was repeated 3 times.
Figure 7A:
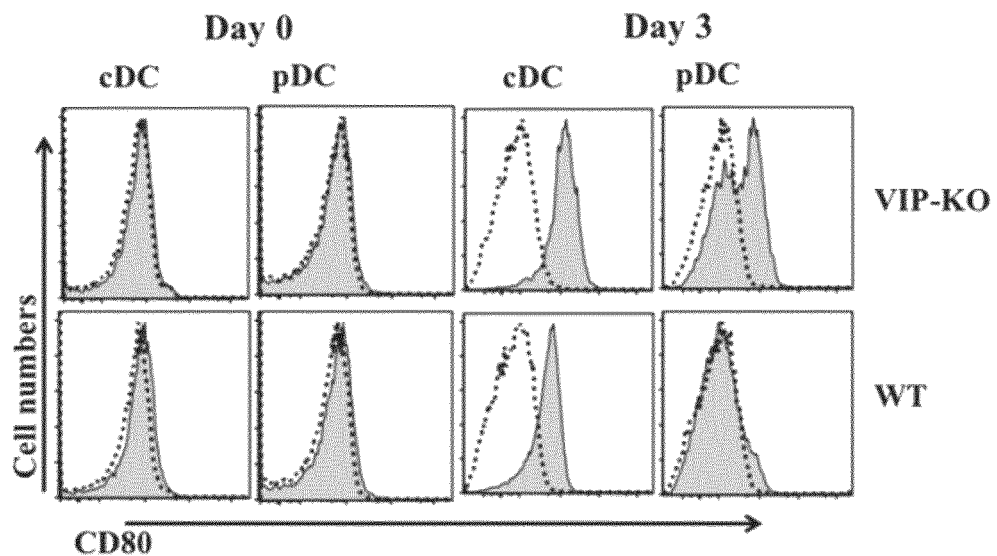
FIG. 7A shows data suggesting higher levels of CD80 expression on DC from VIP-KO mice following mCMV infection. Splenocytes were isolated from VIP-KO and WT mice at baseline and 3, 10 and 17 days after infection with 5×10$^4$ PFU mCMV. Expression patterns of CD80 were analyzed by flow cytometry. Dashed lines represent the staining profile using a isotype-matched control antibody; filled lines represent specific staining.
Figure 7B:
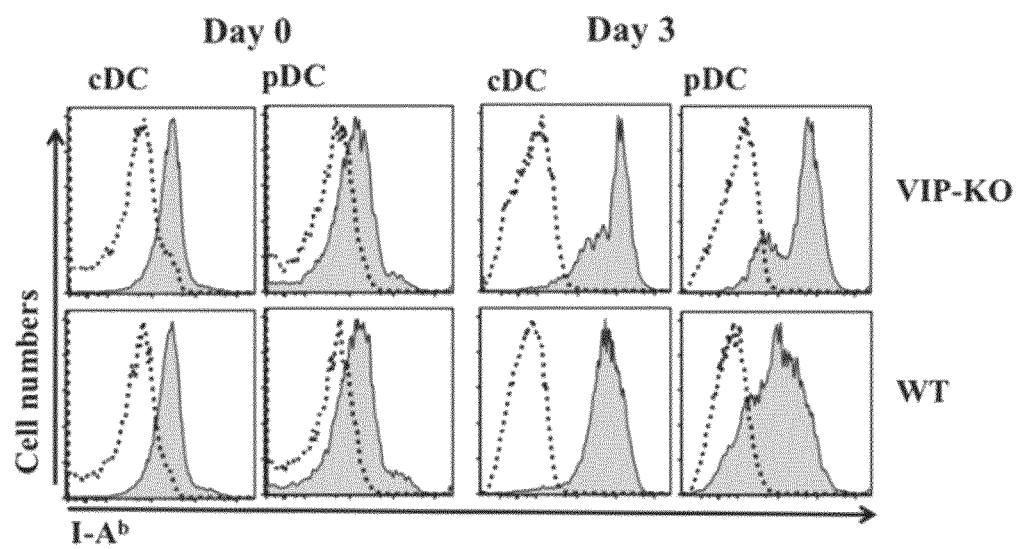
FIG. 7B shows data for MHC-II.
Figure 7C:
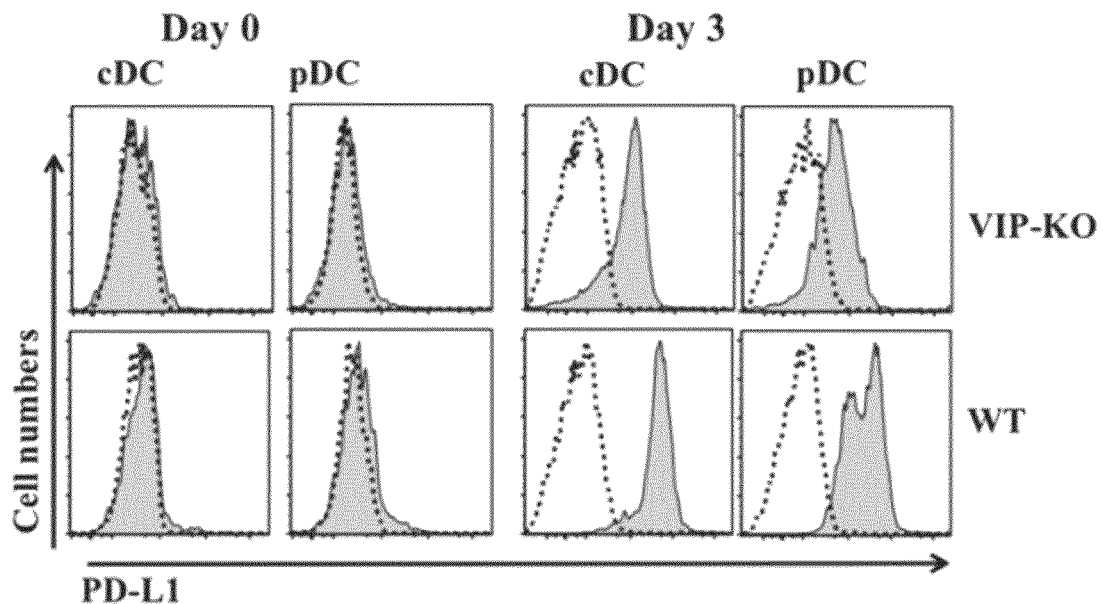
FIG. 7C shows data for PD-L1 on conventional DC (cDC, lineage$^-$, CD11chi, B220$^-$) and plasmacytoid DC (pDC, lineage$^-$, CD11clo, B220$^+$).
Figure 7D:
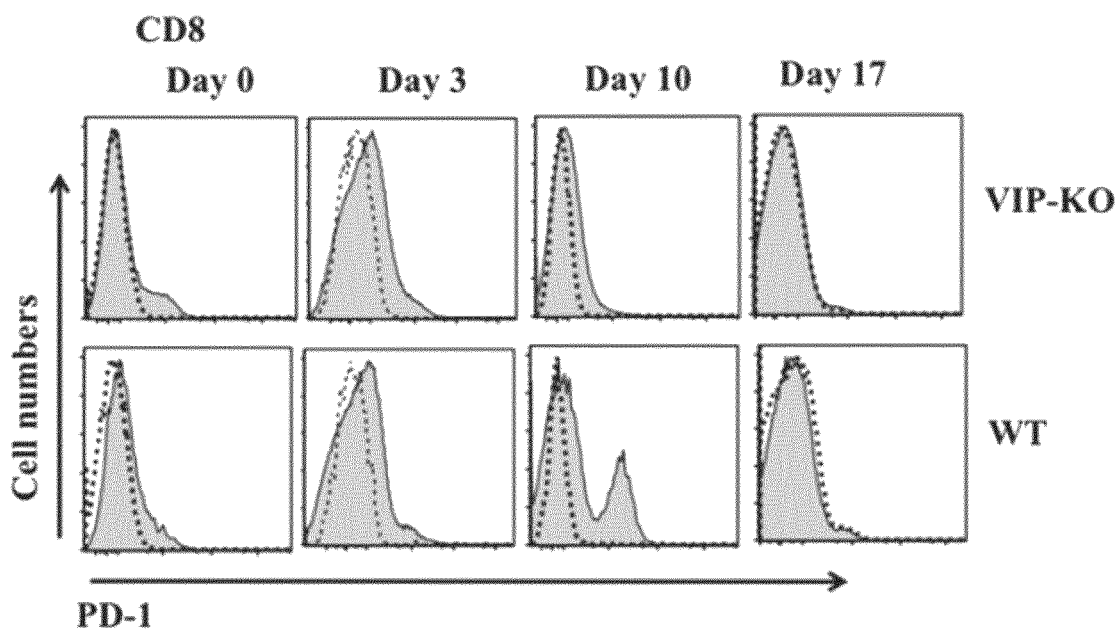
FIG. 7D shows data for the percentages of CD8$^+$ T-cells expressing PD-1.
Figure 8:
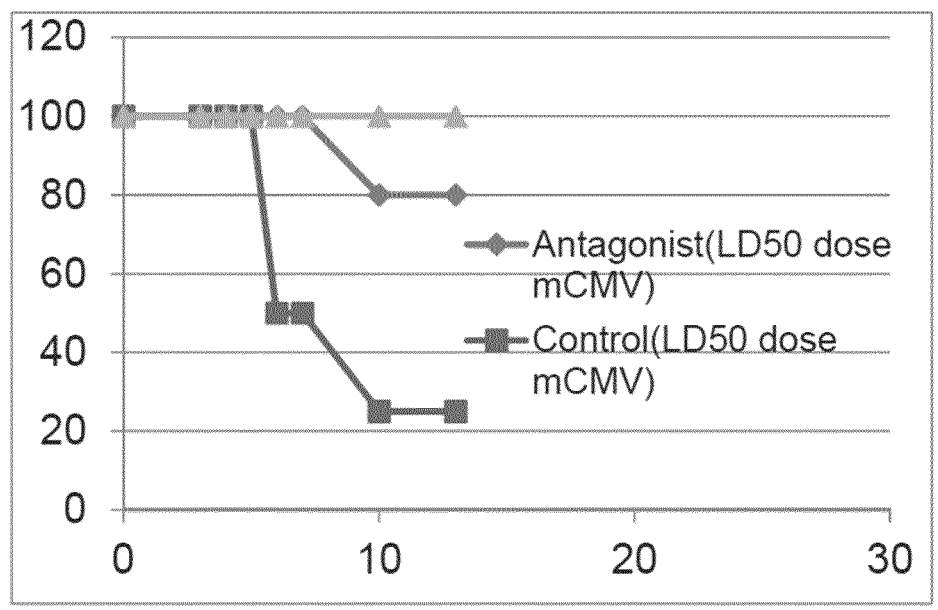
FIG. 8 shows data on the survival of Balb/c mice after i.p. injection with LD50 dose of mCMV in combination with 8 daily subcutaneous doses of VIP antagonist. Control mice received injections of PBS.
Figure 9:
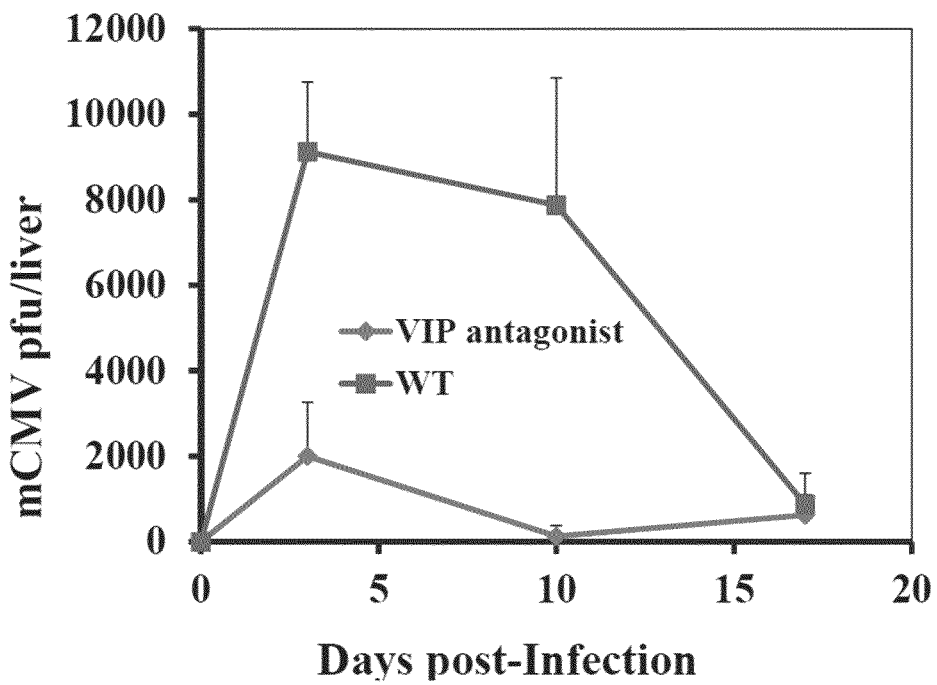
FIG. 9 shows data suggesting that B6 mice treated with VIP antagonist have larger numbers of anti-viral T-cells following mCMV infection.

Absence of VIP Augmented Anti-Viral CD8$^+$ T-Cell Proliferation and Th1/Tc1 Polarization In Vitro To study the effect of VIP on anti-viral immunity in vitro, cultures of T-cells and mCMV-peptide-pulsed DC for MCMV-peptide MHC II-tetramer$^+$ T-cells and for Th1 & Th2 cytokines were analyzed. DC and T-cells were purified from WT or VIP-KO mice, the DC were pulsed with mCMV peptide, and then mixed with T-cells. The numbers of MCMV-peptide MHC II-tetramer$^+$ T-cells generated over 10 days of culture were measured by flow cytometry. Significantly greater numbers of antigen-specific MCMV-peptide MHC II-tetramer$^+$ T-cells were detected after 3 days in cultures of T-cells with DC that had been isolated from mCMV-immune VIP-KO mice compared with similar cells isolated from mCMV-immune WT mice (FIG. 6A). To rule out an effect of VIP synthesized by non-hematopoietic cells on in vitro immune responses to mCMV peptides, donor-derived T-cells and DC were recovered from syngeneic transplants recipients of VIP-KO◊WT or WT◊WT radiation chimeras. Homogeneous cultures of DC and T-cells recovered from VIP-KO◊WT radiation chimera generated more mCMV-peptide-MHC I tetramer$^+$ CD8$^+$ T-cells than cultures of DC and T-cells from WT◊WT radiation chimeras (FIG. 6B), indicating the absence of VIP synthesis by hematopoietic cells in radiation chimeras programmed T-cells and DC towards enhanced cellular immune responses. Supernatants from cultures of T-cells and mCMV-peptide-pulsed DC from WT mice had higher levels of IL-10, and lower levels of IFN-γ compared with supernatants from cultures of T-cells and mCMV-peptide-pulsed DC from VIP-KO mice (FIG. 6C, D). To determine whether synthesis of VIP by T-cells was sufficient to down-regulate immune responses to mCMV, WT T-cells and VIP-KO DC isolated from radiation chimeras originally transplanted with the heterogeneous combination of WT T-cells plus VIP-KO DC and VIP-KO HSC were cultured. In contrast to the larger numbers of mCMV-peptide-MHC-tetramer$^+$ T-cells seen in homogeneous cultures of T-cells and DC from VIP-KO mice, heterogeneous cultures of WT T-cells plus VIP-KO DC generated fewer mCMV-peptide MHC class I-tetramer$^+$ T-cells, similar to cultures of WT T-cells and WT DC, indicating that VIP synthesis by T-cells acts as a dominant negative regulatory mechanism in anti-viral cellular immunity in vitro (FIG. 6B).

Example 5

VIP-KO Mice had Higher Levels of Co-Stimulatory Molecule and MHC Class II Expression on DC and Less PD-1/PD-L1 Expression Compared with WT Mice Following mCMV Infection To explore the mechanism by which the absence of VIP enhanced anti-viral immunity, the expression of co-stimulatory molecules and PD-1/PD-L1 expression in WT and VIP-KO mice following mCMV infection was studied. Prior to mCMV infection, baseline levels of MHC class II, CD80, and PD-L1 expression on DCs, and PD-1 expression on CD4 and CD8 T-cells were similar comparing WT with VIP-KO mice (FIG. 7). VIP-KO mice had a marked up-regulation of CD80 and MHC class II expression on cDC and pDC 3 days after mCMV infection compared with the corresponding DC subsets from mCMV-infected WT mice. Of note, the absence of VIP expression had a significant impact on the up-regulation of co-inhibitory molecules and ligands that normally follows mCMV infection: PD-L1 expression was up-regulated 3 days after mCMV infection in DC from WT but not VIP-KO mice, while WT CD8$^+$ T-cells showed a striking up-regulation of PD-1 expression on day 10 after mCMV infection that was not seen in CD8$^+$ T-cells from VIP-KO mice (FIG. 7).

Methods

Mice

B6 strain (H-2Kb, CD45.2, CD90.2) vasoactive intestinal peptide/peptide histidine isoleucine (VIP/PHI) knockout (KO) mice (VIP-KO) are disclosed in Li et al., J Immunol 183:7799-7809. Both male and female VIP KO mice were used in experiments, using syngenic siblings as wild-type (WT) controls. Congenic strains of B6 mice were purchased from Jackson Laboratory (Bar Harbor, Me.) (H-2Kb, CD45.1, CD90.2) or were bred at the Emory University Animal Care Facility (Atlanta, Ga.) (H-2Kb, CD45.1/CD45.2). All mice were 8-10 weeks old. Procedures conformed to the Guide for the Care and Use of Laboratory Animals, and were approved by the Emory University Institutional Animal Care and Use Committee (IACUC). According to IACUC guidelines, any mouse that lost 25% bodyweight was euthanized and recorded as dying on the following day for statistical analysis.

Donor Cell Preparation for Transplantation

Bone marrow transplantation was performed to create chimeric mice with hematopoietic cells from VIP-KO donors or WT donors (control). Femora, tibia, and spleens were obtained from VIP-KO or WT mice. Bone marrow cells were harvested by flushing the specimens with sterile RPMI-1640 containing 1% heat-inactivated fetal calf serum (RPMI/FCS). T-cells were purified from splenocytes by negative selection using a cocktail of biotinylated non-T-cell antibodies (anti-CD11b, B220, DX5, and Ter119), streptavidin microbeads and immuno-magnetic separation (MACS, Miltenyi Biotech, Auburn, Calif.). The average purity of CD3$^+$ T-cells was 95%. Lineage—(CD3, CD4, CD8, Gr-1, CD11b, I-Ab, DX5, B220, TER119 and CD19) c-kit$^+$ sca-1$^+$ hematopoietic stem cells (HSC) and lineage—(CD3, DX5, IgM, TER119 and CD19) CD11c$^+$ DC from donor BM were purified using a Becton Dickinson FACS Aria cell sorter. Purity of FACS-purified HSC and DC averaged 93% and 97%, respectively.

Radiation Chimeras and Stem Cell Transplantation.

On day −1, 8-10 week old male B6 CD45.1 congenic mice were irradiated with two fractions of 5.5 Gy for a total of 11 Gy (40). On day 0, irradiated mice received 5×10$^6$ TCD-BM cells plus 3×10$^5$ MACS purified splenic T-cells via tail vein injection. Some experiments used an alternate approach, transplanting a combination of 5×10$^3$ HSC, 5×10$^4$ DC, plus 3×10$^5$ T-cells. Mice were monitored for signs of severe infection including fur texture, posture, activity, skin integrity, and weight loss. Each transplant group was followed for at least 100 days. Donor cell chimerism in peripheral blood was determined 2 months after transplantation, and was typically ≥95%. Chimeric mice were then used in vaccination and mCMV infection studies.

Virus and Immunization.

The Smith strain of mCMV passaged in vivo in salivary glands and frozen in aliquots in liquid nitrogen. WT and VIP-KO mice, as well as chimeric mice with hematopoietic cells from WT and VIP-KO donors, were given either $5 \times 10^4$ (LD10; low dose) or $1 \times 10^5$ (LD 50; high dose) plaque-forming unit (PFU) mCMV by intraperitoneal injection and then monitored for signs of illness including hunched posture, decreased activity, and weight loss. Mice were vaccinated intraperitoneally with $1 \times 10^6$ colony-forming unit (CFU) Lm-MCMV, a Listeria monocytogenes which has been rendered non-pathogenic by knock-out of bacterial genes associated with virulence and engineered to express the mCMV H-2Db immuno-dominant peptide M45 aa-985~993-HGIRNASFI (SEQ ID NO: 1). The vaccine was prepared and supplied by Cerus Corporation (Concord, Calif.).

Analysis of Peripheral Blood and Spleen Samples.

Blood and spleen samples were obtained on 3, 7, 10, 14, 17 and 21 days after vaccination or following mCMV infection. Leukocytes, red blood cells and platelets were counted using a Beckman Coulter automated counter. Blood and spleen samples were depleted of red blood cells by ammonium chloride lysis and washed twice. NK, NK-T, and T-cell subsets were enumerated using CD3 PE/PE-Cy7/FITC, CD4 PE-Alexa610/PE-Alexa700, CD8 PE-Cy7/PerCP, CD62L FITC/APC, CD25 APC-Cy7, CD44 PE-Cy5, CD69 PE-Cy7, PD-1 PE, and NK1.1 PE (Pharmingen). Cells were stained with monoclonal antibodies specific for congenic markers CD45.2, CD45.1, CD90.1 and CD90.2 to determine donor chimerism. APC labeled mCMV M45 aa-985~993-peptide-HGIRNASFI-H-2Db tetramer was obtained from the Emory Tetramer Core Facility. All samples were analyzed on a FACS Canto (Beckon Dickinson, San Jose, Calif.) and list mode files were analyzed using FlowJo software (Tree Star, Inc. 2007). Samples for flow cytometric analysis of mCMV-peptide-MHC-I tetramer$^+$ T-cells (tetramer$^+$ T-cells) were gated for lymphocytes in the area of FSC and SSC, and setting a gate for tetramer$^+$ T-cells such that 0.01% of control (non-immune) CD8$^+$ T-cells were positive. Flow cytometric analyses of the Treg-associated molecule PD-1, the co-stimulatory molecule ICOS, the adhesion molecule CD62L, activation markers CD25 and CD69, intracellular cytokines (IFN-γ, TNF-α, IL4 and IL-10), and DC markers (I-Ab, CD80, and PD-L1) were analyzed.

In Vivo Killing Assay.

Naive splenocytes were harvested from CD45.1$^+$/CD45.2$^+$ heterozygous C57BL/6 mice and pulsed with 3 μM mCMV M45 aa-985~993-HGIRNASFI (SEQ ID NO: 1) peptide in RPMI 1640 containing 3% FBS for 90 min at 37° C., and washed three times with ice-cold media. MCMV peptide-pulsed target splenocytes and non-pulsed splenocytes from CD45.1$^+$ B6 congenic mice were mixed together in equal parts $40 \times 10^6$ total target cells per mouse were injected i.v. into CD45.2$^+$ VIP-KO or WT C57BL/6 mice that had been infected 9 days earlier with low dose (LD10) mCMV, or injected into non-infected WT control mice Sixteen hours following injection of target cells, recipients were sacrificed, splenocytes harvested, and the numbers of mCMV peptide-pulsed CD45.1$^+$/CD45.2$^+$ and non-pulsed CD45.1$^-$ target cells quantified by FACS analysis. Immune mediated killing of mCMV peptide pulsed targets was calculated by first dividing the percentage of peptide-pulsed or non-pulsed targets recovered from the spleen of mCMV-immune mice with the mean percentage of the corresponding population of peptide-pulsed or non-pulsed targets from non-immune mice (ratio of immune killing). The specific anti-viral in vivo lytic activity for individual mice were calculated by the formula: (1−(ratio of immune killing mCMV-peptide pulsed-target cells/ratio of immune killing non-pulsed target cells))×100.

In Vitro Measurements of Immune Responses to mCMV Peptide.

WT mice, VIP-KO mice, and mice engrafted with either WT or VIP-KO donor cells were infected with low dose mCMV and splenocytes were harvested 15 days later. Splenic DC and T-cells were purified by FACS and MACS, respectively. DC were plated at $2 \times 10^5$ cells/mL in 12-well plates and centrifuged (300×g for 30 min) with 3 μM mCMV peptide. After centrifugation, DC were washed 3 times with PBS, resuspended in complete medium, and incubated with $2 \times 10^6$ T-cells at 37° C. for 3 or 7 days. Cells were treated with Golgi Stop (Pharmingen, San Jose, Calif.) during the last 6 hours of culture. Cells were then harvested from culture plates and stained with fluorescently-labeled antibodies against DC and T-cell lineage markers, permeabilized, and stained with antibodies against IL-10 and IFN-γ, and analyzed by flow cytometry, using isotype-matched control antibodies to set the gates for distinguishing positive intracellular staining. Harvested culture media was stored at −20° C. until use for cytokine analysis by ELISA (OptEIA ELISA sets for IL-10 and IFN-γ; BD Biosciences). ELISA plates were read using a SpectraMax 340PC spectrophotometer (Molecular Devices, Sunnyvale, Calif.).

NK Cell Lytic Activity.

YAC-1 cells, a sensitive target for NK cells, were labeled with 37 MBq of Na51CrO4 at 37° C. for 90 min and washed twice with warm RPMI 1640 medium. The labeled target cells ($1 \times 10^4$) were co-cultured with effector splenocytes (containing NK cells) at various ratios of effectors: targets (100:1, 50:1, and 25:1) in a final volume of 0.2 ml fresh medium in 96-well round bottom microplates. The plates were incubated for 4 hours at 37° C. with 5% $CO_2$. The amount of $^{51}Cr$ released in 0.1 ml supernatant was measured by a well-type gamma counter (Beta Liquid Scintillation Counter, EG&G Wallac, Perkin-Elmer, Ontario, Canada). Specific cytotoxicity was calculated as: % $^{51}Cr$ release=100×(cpm experimental−cpm spontaneous release)/(cpm maximum release−cpm spontaneous release).

Determination of Liver Viral Load.

Livers were collected from CMV-infected recipients, homogenized, and centrifuged. Serially diluted supernatants were added to 3T3 confluent monolayers in 24-well tissue culture plates and incubated for 90 minutes at 37° C. and 5% $CO_2$, then over layered with 1 mL 2.5% methylcellulose in DMEM and returned to the incubator. After 4 days, the methylcellulose was removed and the 3T3 confluent monolayers were stained with methylene blue. MCMV plaques were directly counted under a light microscope (Nikon, Melville, N.Y.) PFUs were calculated.

The invention claimed is:

1. A method of treating a human subject diagnosed with leukemia comprising administering bone marrow cells in combination with an effective amount of a composition consisting of a vasoactive intestinal peptide (VIP) antagonist, wherein the VIP antagonist is a peptide antagonist to the subject in need thereof, wherein treatment is to treat leukemia; wherein the VIP antagonist is a peptide having a C-terminal amide and is optionally modified with hydrocarbon or polyethylene glycol groups and wherein the peptide has the sequence of SEQ ID NO: 9 wherein X is M; and wherein the bone marrow cells comprise CD8+T cells.

2. The method of claim 1, wherein the bone marrow cells are purified hematopoietic stem cells.

3. The method of claim 1, wherein the bone marrow cells are HLA matched or mis-matched allogeneic cells.

4. The method of claim 1, wherein the bone marrow cells are syngeneic cells.

5. The method of claim 1, wherein the bone marrow cells are autologous cells.

6. A method of treating leukemia comprising administering an effective amount of a composition consisting of a vasoactive intestinal peptide (VIP) antagonist, wherein the VIP antagonist is a peptide antagonist, to a human subject diagnosed with leukemia in combination with transplanting hematopoietic stem cells; wherein the VIP antagonist is a peptide having a C-terminal amide and is optionally modified with hydrocarbon or polyethylene glycol groups and wherein the peptide has the sequence of SEQ ID NO: 9 wherein X is M; and wherein the hematopoietic stem cells comprise CD8+ T cells.

7. The method of claim 6, wherein the hematopoietic stem cells derived from the subject or a donor.

* * * * *

SEQUENCE LISTING

<160> NUMBER OF SEQ ID NOS: 11

<210> SEQ ID NO 1
<211> LENGTH: 170
<212> TYPE: PRT
<213> ORGANISM: Homo sapiens

<400> SEQUENCE: 1

Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
            20                  25                  30

Ser Ala Leu Arg Leu Gly Asp Arg Ile Pro Phe Glu Gly Ala Asn Glu
        35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Ser Asn Ile Ser Glu Asp Pro Val Pro Val Lys Arg His Ser Asp Ala
        115                 120                 125

Val Phe Thr Asp Asn Tyr Thr Arg Leu Arg Lys Gln Met Ala Val Lys
    130                 135                 140

Lys Tyr Leu Asn Ser Ile Leu Asn Gly Lys Arg Ser Ser Glu Gly Glu
145                 150                 155                 160

Ser Pro Asp Phe Pro Glu Glu Leu Glu Lys
                165                 170

<210> SEQ ID NO 2
<211> LENGTH: 169
<212> TYPE: PRT
<213> ORGANISM: Homo sapiens

<400> SEQUENCE: 2

Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
            20                  25                  30

Ser Ala Leu Arg Leu Gly Asp Arg Ile Pro Phe Glu Gly Ala Asn Glu
        35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Asn Ile Ser Glu Asp Pro Val Pro Val Lys Arg His Ser Asp Ala Val
        115                 120                 125

Phe Thr Asp Asn Tyr Thr Arg Leu Arg Lys Gln Met Ala Val Lys Lys
    130                 135                 140

Tyr Leu Asn Ser Ile Leu Asn Gly Lys Arg Ser Ser Glu Gly Glu Ser

```
                145                 150                 155                 160
Pro Asp Phe Pro Glu Glu Leu Glu Lys
                165

<210> SEQ ID NO 3
<211> LENGTH: 28
<212> TYPE: PRT
<213> ORGANISM: Homo sapiens

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 29
<212> TYPE: PRT
<213> ORGANISM: Homo sapiens

<400> SEQUENCE: 4

Tyr Phe Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 23
<212> TYPE: PRT
<213> ORGANISM: Homo sapiens

<400> SEQUENCE: 5

Phe Thr Asp Asn Tyr Thr Arg Leu Arg Lys Gln Met Ala Val Lys Lys
1               5                   10                  15

Tyr Leu Asn Ser Ile Leu Asn
            20

<210> SEQ ID NO 6
<211> LENGTH: 28
<212> TYPE: PRT
<213> ORGANISM: Homo sapiens

<400> SEQUENCE: 6

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 7
<211> LENGTH: 6
<212> TYPE: PRT
<213> ORGANISM: Homo sapiens

<400> SEQUENCE: 7

Lys Pro Arg Arg Pro Tyr
1               5

<210> SEQ ID NO 8
<211> LENGTH: 22
<212> TYPE: PRT
<213> ORGANISM: Homo sapiens

<400> SEQUENCE: 8
```

```
Thr Asp Asn Tyr Thr Arg Leu Arg Lys Gln Met Ala Val Lys Lys Tyr
1               5                   10                  15

Leu Asn Ser Ile Leu Asn
            20

<210> SEQ ID NO 9
<211> LENGTH: 28
<212> TYPE: PRT
<213> ORGANISM: Homo sapiens
<220> FEATURE:
<221> NAME/KEY: misc_feature
<222> LOCATION: (17)..(17)
<223> OTHER INFORMATION: Xaa can be any naturally occurring amino acid

<400> SEQUENCE: 9

Lys Pro Arg Arg Pro Tyr Thr Asp Asn Tyr Thr Arg Leu Arg Lys Gln
1               5                   10                  15

Xaa Ala Val Lys Lys Tyr Leu Asn Ser Ile Leu Asn
            20                  25

<210> SEQ ID NO 10
<211> LENGTH: 27
<212> TYPE: PRT
<213> ORGANISM: Homo sapiens

<400> SEQUENCE: 10

His Phe Asp Ala Val Phe Thr Asn Ser Tyr Arg Lys Val Leu Lys Arg
1               5                   10                  15

Leu Ser Ala Arg Lys Leu Leu Gln Asp Ile Leu
            20                  25

<210> SEQ ID NO 11
<211> LENGTH: 32
<212> TYPE: PRT
<213> ORGANISM: Homo sapiens

<400> SEQUENCE: 11

Thr Asp Ser Tyr Ser Arg Tyr Arg Lys Gln Met Ala Val Lys Lys Tyr
1               5                   10                  15

Leu Ala Ala Val Leu Gly Lys Arg Tyr Lys Gln Arg Val Lys Asn Lys
            20                  25                  30
```